(12) United States Patent
Borody

(10) Patent No.: US 10,195,235 B2
(45) Date of Patent: Feb. 5, 2019

(54) METHODS FOR TREATING ULCERATIVE COLITIS

(71) Applicant: Crestovo Holdings LLC, Greenwich, CT (US)

(72) Inventor: Thomas Julius Borody, Five Dock (AU)

(73) Assignee: Crestovo Holdings LLC, Somerville, MA (US)

( * ) Notice: Subject to any disclaimer, the term of this patent is extended or adjusted under 35 U.S.C. 154(b) by 0 days.

(21) Appl. No.: 15/791,868

(22) Filed: Oct. 24, 2017

(65) Prior Publication Data

US 2018/0125899 A1 May 10, 2018

Related U.S. Application Data

(63) Continuation of application No. PCT/US2017/045092, filed on Aug. 2, 2017.

(60) Provisional application No. 62/370,508, filed on Aug. 3, 2016.

(51) Int. Cl.

| A61K 39/02 | (2006.01) |
| A61K 49/00 | (2006.01) |
| A61K 39/00 | (2006.01) |
| A61K 35/74 | (2015.01) |
| A61K 35/741 | (2015.01) |
| A61P 1/04 | (2006.01) |
| A61K 35/37 | (2015.01) |
| A61K 35/00 | (2006.01) |

(52) U.S. Cl.
CPC .............. *A61K 35/74* (2013.01); *A61K 35/37* (2013.01); *A61K 35/741* (2013.01); *A61P 1/04* (2018.01); *A61K 2035/115* (2013.01)

(58) Field of Classification Search
CPC ................................ A61K 39/00; A61K 39/02
USPC ...................................... 424/9.1, 9.2, 234.1
See application file for complete search history.

(56) References Cited

U.S. PATENT DOCUMENTS

| 3,192,116 A | 6/1965 | Möse et al. |
| 3,320,130 A | 5/1967 | Henry |
| 3,713,836 A | 1/1973 | Carlsson |
| 4,098,728 A | 7/1978 | Rosenblatt |
| 4,332,790 A | 6/1982 | Sozzi et al. |
| 4,335,107 A | 6/1982 | Snoeyenbos et al. |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,599,795 A | 2/1997 | McCann et al. |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |

(Continued)

FOREIGN PATENT DOCUMENTS

| AU | 2001276160 B2 | 6/2007 |
| CA | 1333564 | 12/1994 |

(Continued)

OTHER PUBLICATIONS

Shi, Y., et al. PLOS one, vol. 11, No. 6, e0157259, pp. 1-18, Jun. 13, 2016.*
"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems, 10th Revision (ICD-10)—WHO Version, Chapter 1*, pp. 1 (2016) <www.apps.who.int/classifications/icd10/browse/2016/en#/I>.
"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).

(Continued)

*Primary Examiner* — Rodney P Swartz
(74) *Attorney, Agent, or Firm* — Arnold & Porter Kaye Scholer LLP; David R. Marsh

(57) ABSTRACT

The present disclosure provides methods and treatment regimens for treating ulcerative colitis in a subject in need thereof. In particular, the methods described herein comprise treating a subject in need thereof with a treatment regimen comprising the administration of a pharmaceutical composition comprising live non-pathogenic fecal bacteria for at least 8 weeks and at least three times per week. In an aspect, the subject in need thereof exhibits a Mayo endoscopy score of 3 or lower. In some aspects, the subject in need thereof has no concomitant corticosteroid use during said method and has no corticosteroid use immediately prior to commencing said method.

37 Claims, 11 Drawing Sheets

(56) References Cited

U.S. PATENT DOCUMENTS

| | | |
|---|---|---|
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |
| 2018/0036352 A1 | 2/2018 | Borody |

FOREIGN PATENT DOCUMENTS

| | | |
|---|---|---|
| CA | 2 391 422 A1 | 1/2004 |
| CN | 1561387 A | 1/2005 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 800 688 A1 | 6/2007 |
| EP | 1 514 572 B1 | 12/2008 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2011/152566 A2 | 12/2011 |
| WO | WO 2012/016287 A2 | 2/2012 |

(56) References Cited

FOREIGN PATENT DOCUMENTS

| WO | WO 2012/045150 A1 | 4/2012 |
|---|---|---|
| WO | WO 2012/122478 A1 | 9/2012 |
| WO | WO 2012/016287 A3 | 11/2012 |
| WO | WO 2013/037067 A1 | 3/2013 |
| WO | WO 2013/090825 A1 | 6/2013 |
| WO | WO 2014/078911 A1 | 5/2014 |
| WO | WO 2014/152338 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |

OTHER PUBLICATIONS

"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report.pdf>.
"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 <http://www.cdc.gov/HAI/organisms/cdiff/Cdiff_faqs_HCP.html>.
"Functional Anatomy of Prokaryotic and Eukaryotic Cells," printed Mar. 16, 2017 <http://classes.midlandstech.edu/carterp/courses/bio225/chap04/lecture2.htm>.
"Monilia," Def. 1, Stedman's Medical Dictionary, n.d., Web, Nov. 22, 2005.
"Probiotic," Def. 1, MSN Encarta—Dictionary, Encarta, n.d., Web, Dec. 1, 2005.
Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).
Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).
Acha et al., "Changes of viability and composition of the *Escherichia coli* flora in faecal samples during long time storage," Journal of Microbiological Methods, Elsevier, 63(3):229-238 (2005).
Agrawal et al., "'Global warming' to *Mycobacterium avium* subspecies *paratuberculosis*," *Future Microbiol*, 9(7):829-832 (2014).
Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gasyroenterol*, 146(5)(Suppl 1):S42-43 (2014).
Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao et al., "A Purgative Action of Barbaloin Is Induced by *Eubacterium* sp. Strain BAR, a Human Intestinal Anaerobe, Capable of Transforming Barbaloin to Aloe-Emodin Anthrone," Biol. Pharm., 19(1):136-138 (1996).
Al-Eidan et al., "Clostridium difficile-associated diarrhoea in hospitalised patients," *J. Clin. Pharm. Ther.*, 25(2):101-109 (2000).
Al-Nassir et al., "Comparison of Clinical and Microbiological Response to Treatment of Clostridium difficile-Associated Disease with Metronidazole and Vancomycin," *Clin Infect Dis.*, 47(0:56-62 (2008).
Anand et al., "Epidemiology, clinical manifestations, and outcome of Clostridium difficile-associated diarrhea," *Am J Gastroenterol.*, 89(4):519-23 (1994).
Ananthakrishnan et al., "Excess hospitalisation burden associated with Clostridium difficile in patients with inflammatory bowel disease," *Gut*, 57(2):205-210 (2007).
Anderson et al., "Systematic review: faecal microbiota transplantation in the management of inflammatory bowel disease," *Aliment. Pharmacol. Ther.*, 36:503-16 (2012).
Andoh et al., "Terminal restriction fragment polymorphisum analyses of fecal microbiota in five siblings including two with ulcerative colitis," *Journal of Clinical Gastroenterology*, 2:343-345 (2009).
Andrews et al., "'Putting back the bugs': Bacterial Treatment Relieves Chronic Constipation and Symptoms of Irritable Bowel Syndrome," *Med. J. Aust.*, 159(9):633-634 (1993).
Andrews et al., "Bacteriotherapy for Chronic Constipation—A Long Term Follow-Up," *Gastroenterol*, 108:A563 Abstract (1995).
Andrews et al., "Chronic Constipation (CC) may be reversed by Bacteriotherapy," *Gastroenterol*, 106:A459 (1994).
Andrews et al., "Chronic constipation reversed by restoration of bowel flora. A case and a hypothesis," *European Journal of Gastroenterology & Hepatology*, 4:245-247 (1992).
Anorexia nervosa, Encyclopedia Index A, healthAtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent *Clostridium difficile* Infection," *Gastroenterology*, 138(5):S1-S5 (2010).
Aroniadis et al., "Intestinal Microbiota and the Efficacy of Fecal Microbiota Transplantation in Gastrointestinal Disease," Gastroenterology and Hepatology, 10(4): 230-7 (2014).
Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).
Atarashi et al., "Induction of Colonic Regulatory T Cells by Indigenous *Clostridium* Species," *Science*, 331(6015):337-341, published online Dec. 23, 2010.
Atarashi et al., "$T_{reg}$ induction by a rationally selected mixture of *Clostridia* strains from the human microbiota," *Nature*, 500(7461):232-236 (2013).
Atarashi et al., "WS/PP-064-03 Regulation of colonic regulatory T cells by *Clostridium* species," *International Immunology*, 22(Suppl 1, Part 3), pp. 1-3 (2010).
Atarashi et al., WS-064 Mucosal immunity: homeostasis, 14th ICIC Abstract book, 14th International Congress of Immunology, pp. iii131-iii133 (2010).
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Hosacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent Clostridium difficile infection," *Anaerobe*, 15(6):285-289 (2009).
Bakken et al., "Treating Clostridium difficile Infection with Fecal Microbiota Transplantation," *Clinical Gasfroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Belkaid et al., "Natural regulatory T cells in infectious disease," *Nature Immunology*, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Blaser et al., "What are the consequences of the disappearing human microbiota?" *Nat. Rev. Microbiol.*, 7(12):887-894 (2009).

(56) References Cited

OTHER PUBLICATIONS

Blaser, "Who are we? Indigenous microbes and the ecology of human diseases," *EMBO Rep*, 7(10):956-960 (2006).

Bolte, "Autism and Clostridium tetani," Medical Hypotheses, 51(2):133-144 (1998).

Bolte, "Therapies for Gastrointestinal and Neurological Disorders," U.S. Appl. No. 60/214,813, filed Jun. 28, 2000.

Borody et al., "Anti-MAP Rescues Anti-TNF Failures for Over 4 Years," *Gastroenterol*, 136(5)Suppl 1:A-681 (2009).

Borody et al., "Anti-MAP Therapy for Pediatric Crohn's Disease," *Am J Gastroenterol*, 108(Suppl 1):S516 (2013).

Borody et al., "Anti-MAP Therapy in the Treatment of Active Crohn's Disease," *J Gastroenterol & Hepatol*, 20(Suppl):A2 (2005).

Borody et al., "Anti-mycobacterial therapy in Crohn's disease heals mucosa with longitudinal scars," *Digestive & Liver Disease*, 39(5):438-444 (2007).

Borody et al., "Anti-*Mycobacterium avium* SS *Paratuberculosis* (MAP) Therapy and Fistula Closure in Patients with Severe Crohn's Disease," *Am J Gast*, A101:S440 (2006).

Borody et al., "Bacteriotherapy in Chronic Fatigue Syndrome (CFS): A retrospective review," *Am J Gastro*, 107(S1):A1481 (2012).

Borody et al., "Bacteriotherapy Using Fecal Flora: toying with human motions" *J. Clin. Gastroenterol.*, 38(6):475-483 (2004).

Borody et al., "Bowel-flora alteration: a potential cure for inflammatory bowel disease and irritable bowel syndrome?" *Med. J. Aust.*, 150:604 (1989).

Borody et al., "Changes in Crohn's Disease Activity Index and C-Reactive Protein Levels During Anti-MAP Therapy," *AM J Gastro*, 104(S3):A1293 (2009).

Borody et al., "Clostridium difficile Complicating Inflammatory Bowel Disease: Pre- and Post-Treatment Findings," *Gastroenterol*, 134(4)Suppl 1:A-361 (2008).

Borody et al., "Could fecal microbiota transplantation cure all Clostridium difficile infections?," *Future Microbiol*, 9:1-3 (2014).

Borody et al., "Entamoeba histolytica: another cause of Crohn's Disease," *AM J Gastro*, 104(S3):A990 (2009).

Borody et al., "Faecal bacteriotherapy (FB) for chronic *C. difficile* (*Cd*) *syndromes*," *J Gastroenterol Hepatol*, 18(Suppl):B8 (Abstract) (2003).

Borody et al., "Fecal bacteriotherapy in the treatment of recurrent C. difficile infection," *UpToDate*, pp. 1-6 (2006).

Borody et al., "Fecal Microbiota Transplantation (FMT) in Multiple Sclerosis (MS)," *AM J Gastro*, 106(S2):A942 (2011).

Borody et al., "Fecal microbiota transplantation and emerging applications," *Nat. Rev. Gastroenterol. Hepatol.*, 9(2):88-96 (2011).

Borody et al., "Fecal microbiota transplantation for *Clostridium difficile* infection: A surgeon's perspective" *Seminars in Colon and Rectal Surgery*, 25:163-166 (2014).

Borody et al., "Fecal microbiota transplantation in gastrointestinal diseases—What practicing physicians should know," *Polish Archives of Internal Medicine*, 125(11):852-858 (2015).

Borody et al., "Fecal microbiota transplantation in the treatment of recurrent Clostridium difficile infection," *UpToDate*, pp. 1-4, (2015).

Borody et al., "Fecal Microbiota Transplantation in Ulcerative Colitis: Review of 24 Years Experience," *Am J Gastro*, 107(Supp 1):A1644 (2012).

Borody et al., "Fecal microbiota transplantation: a new standard treatment option for *Clostridium difficile* infection," *Expert Rev Anti Infect Ther.*, 11(5):447-449 (2013).

Borody et al., "Fecal microbiota transplantation: current status and future directions," *Expert Review of Gastroenterology & Hepatology*, 5(6):653-655 (2011).

Borody et al., "Fecal Microbiota Transplantation: Expanding Horizons for *Clostridium difficile* Infections and Beyond," *Antibiotics*, 4:254-266 (2015).

Borody et al., "Fecal Microbiota Transplantation: Indications, Methods, Evidence, and Future Directions," *Curr Gastroenterol Rep*, 15:337-344 (2013).

Borody et al., "Fecal Microbiota Transplantation: Techniques, Applications, and Issues," *Gastroenterol Clin North Am*, 41:781-803 (2012).

Borody et al., "Irritable Bowel Syndrome and *Dientamoeba fragilis*," *ASM Sydney National Conference*, pp. 4-5 (2002).

Borody et al., "Is Crohn's Disease Ready for Fecal Microbiota Transplantation?," *J Clin Gastroenterol*, 48(7):582-583 (2014).

Borody et al., "Myoclonus-dystonia affected by GI Microbiota?," *AM J Gastro*, 106(S2):A940 (2011).

Borody et al., "Novel appearance of healing mucosa following anti-*Mycobacterium avium paratuberculosis* therapy for Crohn's disease," *J Gastroenterol Hepatol*, 19(Suppl):A210 (2004).

Borody et al., Reversal of Idiopathic Thrombocytopenic Purpura [ITP] with Fecal Microbiota Transplantation [FMT], *AM J Gastro*, 106(S2):A941 (2011).

Borody et al., "Reversal of Inflammatory Bowel Disease (IBD) with Recurrent Faecal Microbiota Transplants (FMT)," *AM J Gastro*, 106(S2):A979 (2011).

Borody et al., "Severe recurrent Crohn's Disease of ileocolonic anastomosis and antimicrobial (anti-mycobacterial therapy)," *Gut*, 55:1211 (2006).

Borody et al., "The GI Microbiome and its Role in Chronic Fatigue Syndrome: a Summary of Bacteriotherapy," ACNEM Journal, 31(3):3-8 (2012).

Borody et al., "Therapeutic faecal microbiota transplantation: current status and future developments," *Curr Opin Gastroenterol*, 30:97-105 (2014).

Borody et al., "Treatment of chronic constipation and colitis using human probiotic infusions," *Proceedings of Prebiotics and Probiotics and the New Foods Conference*, 2-4:228 Abstract (2001).

Borody et al., "Treatment of First-time Clostridium difficile Infection with Fecal Microbiota Transplantation," Poster Presentation, *2015 ACG Annual Scientific Meeting*, Honolulu, Hawaii, USA (2015).

Borody et al., "Treatment of Severe Constipation Improves Parkinson's Disease (PD) Symptoms," *Am J Gastro*, 104(S3):A999 (2009).

Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).

Borody et al., Treatment of Severe Crohn's Disease Using Rifabutin-Macrolide-Clofazimine Combination—Results at 38-43 Months, *J Gastroenterol & Hepatol*, 15(Suppl):J102 (2000).

Borody et al., "Treatment of Severe Crohn's disease using antimycobacterial triple therapy—approaching a cure?," *Digest Liver Dis*, 34(1):29-38 (2002).

Borody et al., "Treatment of ulcerative colitis using fecal bacteriotherapy," *J. Clin. Gastroenterol.*, 37(1):42-47 (2003).

Borody, "Bacteriotherapy for Chronic Fatigue Syndrome—A Long Term Follow-Up Study," Proceedings of ACMA Complementary Medicine Sydney, p. 1 (1995).

Borody, "Flora Power—Fecal Bacteria Cure Chronic C. difficile Diarrhoea," *Am J Gastroenterol*, 95(11):3028-3029 (2000).

Borody, "Is the Infected Patient too 'Difficile' to Treat?," The Australian Society for Microbiology 2009 Perth, SY03 & SY03.1, p. 27 & 56, (2009).

Borody, "Letter to the Editor—Response to Drs. Famularo et al.," *AJG*, 96(7):2262-2264 (2001).

Borriello, "Clostridial Disease of the Gut" Clinical Infectious Diseases, The University of Chicago, 20(Suppl 2):S242-S250 (1995).

Bowden et al., "Pseudomembraneous enterocolitis: mechanism of restoring floral homeostasis," *Am Surg.*, 47(4):178-183 (1981).

Brandt et al., "Endoscopic Fecal Microbiota Transplantation: "First-Line" Treatment for Severe Clostridium difficile Infection?" *J. Clin. Gastroenterol.*, 45(8):655-657 (2011).

Brandt et al., "Fecal microbiota transplantation for recurrent *Clostridium difficile* infection," *J Clin Gastroenterol.*, 45(Suppl):S159-S167 (2011).

Brandt et al., "Long-Term Follow-Up Study of Fecal Microbiota Transplantation (FMT) for Ulcerative Colitis (UC)," Am. J. Gastroenterol., 107(Suppl 1):S657 (2012).

Brandt et al., Safety of Fecal Microbiota Transplantation (FMT) in Immunocompromised (Ic) Patients with Inflammatory Bowel Disease (IBD), *Am J Gastroenterol*, 108(Suppl 1):S556 (2013).

(56) References Cited

OTHER PUBLICATIONS

Browne et al., "Culturing of 'unculturable' human microbiota reveals novel taxa and extensive sporulation," *Nature*, 533(7604):543-546 (2016).
Bueche et al., "Quantification of Endospore-Forming Firmicutes by Quantitative PCR with the Functional Gene spo0A," Applied and Environmental Microbiology, 79(17):5302-5312 (2013).
Cano et al., "Revival and identification of bacterial spores in 25-40 million year old Dominican Amber Science," Science, 268(5213):1060-1064 (1995).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk—four states, 2005." *Morbidity and Mortality Weekly Report*, 54(47):1201-1205 (2005).
Chamberlain et al., "MAP-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J. Infect. Dis.*, 197(3):435-438 (2008).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Choi et al., "Fecal Microbiota Transplantation. Current Applications, Effectiveness, and Future Perspectives," Clin. Endosc., 49:257-265 (2016).
Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," PLOS One, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Clancy et al., "Anti-MAP Therapy Induces and Maintains Remission in Severe Crohn's Disease," Ann NY Acad Sci, p. 1 (2005).
Claus et al., "Colonization-induced host-gut microbial metabolic interaction," MBio, 2(2):e00271-00210 (2011).
Claus et al., "Systemic multicompartmental effects of the gut microbiome on mouse metabolic phenotypes," *Mol. Syst. Biol.*, 4(1):219 (2008).
Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).
Collins et al., "The Phylogeny of the Genus *Clostridium*: Proposal of Five New Genera and Eleven New Species Combinations," International Journal of Systematic Bacteriology, pp. 812-826 (1994).
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Herewith.Applied Bacteriology, 34(2):477-483 (1971).
Cutolo et al., "Fecal feedings as a therapy in *Staphylococcus enterocolitis*," NY State J Med, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," J. Med Microbiology, 28:151-154 (1989).
De Giulio et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," *Drug Develop. & Indust. Pharm.*, 31:677-685 (2005).
Dendukuri et al., "Probiotic therapy for the prevention and treatment of Clostridium difficile-associated diarrhea: a systematic review," *CMAJ*, 173 (2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," *Nature*, 449(7164):811-818 (2007).
Dewhirst et al., "Phylogeny of the Defind Murine Microbiota: Altered Schaedler Flora," Applied and Environmental Microbiology, 65(8):3287-3292 (1999).
DuPont, "The search for effective treatment of Clostridium difficile infection," *N Engl J Med.*, 364(5):473-475 (2011).
Eckburg et al., "Diversity of the human intestinal microbial flora," *Science*, 308(5728):1635-1638 (2005).
Eiseman et al., "Fecal enema as an adjunct in the treatment of pseudomembranous enterocolitis," *Surgery*, 44(5):854-859 (1958).
Extended European Search Report dated Apr. 3, 2014, in European Patent Application No. 11813951.8.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," *Can J Gastroenterol.*, 16:A43 (2002).
Fenton et al., "Pseudomembranous colitis associated with antibiotic therapy—an emerging entity," *Can Med Assoc J.*, 111(10):1110-1111 (1974).
Floch et al., "Probiotics and Dietary Fiber, The Clinical Coming of Age of Intestinal Microecology," *J. Clin. Gastroenterology*, 27(2):99-100 (1998).
Floch, "Fecal Bacteriotherapy, Fecal Transplant, and the Microbiome," *J. Clin. Gastroenterol.*, 44(8):529-530 (2010).
Flotterod et al., "Refractory Clostridium difficile infection. Untraditional treatment of antibiotic-induced colitis," *Tidsskr nor Laegeforen*, 111:1364-1365 (1991).
Frank et al., "Molecular-phylogenetic characterization of microbial community imbalances in human inflammatory bowel diseases," *PNAS*, 104(34):13780-13785 (2007).
Frantzen et al., "Empirical evaluation of preservation methods for faecal DNA," *Molecular Ecology*, 7(10):1423-1428 (1998).
Freeman et al., "The changing epidemiology of Clostridium difficile infections," *Clin Microbiol. Rev.*, 23(3):529-549 (2010).
Frese et al., "The evolution of host specialization in the vertebrate gut symbiont Lactobacillus reuteri," *PloS Genet.*, 7(2):e1001314 (2011).
Gaboriau-Routhiau et al., "The Key Role of Segmented Filamentous Bacteria in the Coordinated Maturation of Gut Helper T Cell Responses," *Immunity*, 31(4):677-689 (2009).
Garborg et al., "Results of faecal donor instillation therapy for recurrent Clostridium difficile-associated diarrhoea," *Scand J Infect Dis.*, 42(11-12):857-61 (2010).
Garey et al., "Meta-analysis to assess risk factors for recurrent Clostridium difficile infection," *J. Hosp. Infect.*, 70(4):298-304 (2008).
Gerding, "Management of Clostridium difficile infection: thinking inside and outside the box," *Clin Infect Dis.*, 51(11):1306-13 (2010).
Geuking et al., "Intestinal Bacterial Colonization Induces Mutualistic Regulatory T Cell Respones," *Immunity*, 34:794-806 (2011).

(56) References Cited

OTHER PUBLICATIONS

Gitlin et al., "*Mycobacterium avium* ss paratuberculosis-associated Diseases: Piecing the Crohn's Puzzle Together," *J Clin Gastroenterol*, 46(8):649-655 (2012).

Gough et al., "Systematic review of intestinal microbiota transplantation (fecal bacteriotherapy) for recurrent Clostridium difficile infection," *Clin. Infect. Dis.*, 53(10):994-1002 (2011).

Grehan et al., "Durable alteration of the colonic microbiota by the administration of donor fecal flora," *Journal of Clinical Gastroenterology*, 44(8):551-561 (2010).

Guarner et al., "Gut flora in health and disease," *Lancet*, 361(9356):512-519 (2003).

Gustafsson et al., "The Effect of Faecal Enema on Five Microflora-Associated Characteristics in Patients with Antibiotic-Associated Diarrhoea," *Scandinavian Journal of Gastroenterology*, 34:580-586 (1999).

Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).

Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.

Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).

Hamilton et al., "Standardized Frozen Preparation for Transplantation of Fecal Microbiota for Recurrent Clostridium difficile Infection," Article and Supplementary Material, *Am. J. Gastroenterol.*, 107(5):761-767 (2012).

Hayashi et al., "Phylogenetic Analysis of the Human Gut Microbiota Using 16S rDNA Clone Libraries and Strictly Anaerobic Culture-Based Methods," *Microbiol. Immunol.*, 46(8):535-548 (2002).

Hecker et al., "Fecal Microbiota Transplantation by Freeze-Dried Oral Capsules for Recurrent Clostridium difficile Infection," *Open Forum Infect Dis*, 3(2): 1-2 (2016).

Hellemans et al., "Fecal transplantation for recurrent Clostridium difficile colitis, an underused treatment modality," *Acta Gastroenterol Belg.*, 72(2):269-70 (2009).

Henriksson et al., "Probiotics under the regulatory microscope," *Expert Opin. Drug Saf.*, 4(6):1-9 (2005).

Hensel et al., "Vagal Ascent and Distribution of 125 I-Tetanus Toxin after Injection into the Anterior Wall of the Stomach," *Naunyn-Schmiedeberg's Arch. Pharmacol*, 276:395-402 (1973).

Honda et al., "Regulation of T Cell Responses by Intestinal Commensal Bacteria," *Journal of Intestinal Microbiology*, vol. 25, 2nd Edition:104 (2011).

Hooper et al., "How host-microbial interactions shape the nutrient environment of the mammalian intestine," *Annu. Rev. Nutr.*, 22:283-307 (2002).

Hope et al., "Sporadic colorectal cancer-role of the commensal microbiota," *FEMS Microbiol. Lett.*, 244:1-7 (2005).

Hota et al., "Determining Mortality Rates Attributable to Clostridium difficile Infection," *Emerg. Infect. Dis.*, 18(2):305-307 (2012).

Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.

Hu et al., "Prospective derivation and validation of a clinical prediction rule for recurrent Clostridium difficile infection," *Gastroenterology*, 136:1206-1214 (2009).

Huang et al., "Once-daily propranolol extended-release tablet dosage form: formulation design and in vitro/in vivo investigation," *European J. of Pharm. & Biopharm.*, 58:607-614 (2004).

Huttenhower et al., "Structure, function and diversity of the healthy human microbiome," The Human Microbiome Project Consortium, *Nature*, 486:207-214 (2012).

Immunology in the 21st Century: Defeating Infection, Autoimmunity, Allergy, and Herewith.Cancer, ICI 2010 Wrap-up Report, 14th International Congress of Immunology, pp. 1 (2010).

Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowels/chrohns.html>.

International Preliminary Examination Report completed Nov. 19, 2002, in International Application No. PCT/AU2001/000907, 19 pgs.

International Preliminary Report on Patentability completed Dec. 12, 2012, in International No. PCT/AU2011/000987, 35 pgs.

International Preliminary Report on Patentability completed Mar. 12, 2015, in International Application No. PCT/AU2013/001362, 29 pgs.

International Preliminary Report on Patentability dated Sep. 10, 2013, in International Application No. PCT/US2012/028484, 10 pgs.

International Search Report and Written Opinion dated Aug. 8, 2016, in International Application No. PCT/US2016/032695, 10 pgs.

International Search Report and Written Opinion dated Feb. 5, 2014, in International Application No. PCT/AU2013/001362, 17 pgs.

International Search Report and Written Opinion dated Jul. 31, 2014, in International Application No. PCT/US2014/027391, 16 pgs.

International Search Report and Written Opinion dated Oct. 28, 2011, in International No. PCT/AU2011/000987, 18 pgs.

International Search Report dated Aug. 10, 2012, in International Application No. PCT/US2012/028484, 7 pgs.

International Search Report dated Jul. 29, 2014, in International Application No. PCT/AU2014/000478, 7 pgs.

International Search Report dated Sep. 22, 2017, in International Application No. PCT/US2017/040591, 12 pgs.

Irrgang et al., "The historical Development of Mutaflor therapy," Ardeypharm GmbH, pp. 1-38 (1988) <http://www.ardeypharm.de/pdfs/en/mutaflor_historical_e.pdf?>.

Irritable Bowel Syndrome (IBS), Health A to Z, InteliHealth, pp. 1-4, n.d., Web, Oct. 23, 2005 <http://www.intelihealth.com>.

Issa et al., "Clostridium difficile and Inflammatory Bowel Disease," *Inflamm Bowel Dis.*, 14(10):1432-1442 (2008).

Issa et al., "Impact of Clostridium difficile on inflammatory bowel disease," *Clin. Gastroenterol. Hepatol.*, 5(3):345-351 (2007).

Itoh et al., "Characterization of clostridia isolated from faeces of limited flora mice and their effect on caecal size when associated with germ-free mice," *Laboratory Animals*, 19:111-118 (1985).

Itoh et al., "Intestinal bacteria antagonistic to *Clostridium difficile* in mice," *Laboratory Animals*, 21:20-25 (1987).

Ivanov et al., "Specific Microbiota Direct the Differentiation of IL-17-Producing T-Helper Cells in the Mucosa of the Small Intestine," *Cell Host & Microbe*, 4:337-349 (2008).

Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).

Janeway et al., "Adaptive Immunity to Infection," *Immunobiology*, 6th Edition, Chapter 10, pp. 414 (2005).

Janeway, Jr. et al., "Autoimmune responses are directed against self antigens," *Immunobiology: The Immune System in Health and Disease*, 5th Edition, pp. 1-4 (2001).

Jarvis et al., "National point prevalence of Clostridium difficile in US health care facility inpatients, 2008," *Am. J. Infect. Control*, 37:263-270 (2009).

Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).

Johnson et al., "Rifaximin Redux: Treatment of recurrent Clostridium difficile infections with Rifaximin immediately post-vancomycin treatment," *Anaerobe*, 15(6):290-291 (2009).

(56) References Cited

OTHER PUBLICATIONS

Kageyama et al., "Emendation of genus *Collinsella* and proposal of *Collinsella stercoris* sp. nov. and *Collinsella intestinalis* sp. nov.," *International Journal of Systematic and Evolutionary Microbiology*, 50:1767-1774 (2000).

Kageyama et al., "Phylogenetic and phenotypic evidence for the transfer of Eubacterium aerofaciens to the genus *Collinsella* as *Collinsella aerofaciens* gen. nov., comb. nov.," *International Journal of Systematic Bacteriology*, 49:557-565 (1999).

Kakihana et al., "Fecal microbiota transplantation for patients with steriod-resistant acute graft-versus-host disease of the gut," *Blood*, 128(16):2083-2088 (2016).

Kamboj et al., "Relapse versus reinfection: surveillance of Clostridium difficile infection," *Clin Infect Dis.*, 53(10):1003-1006 (2011).

Kang et al., "Microbiota Transfer Therapy alters gut ecosystem and improves gastrointestinal and autism symptoms: an open-label study," *Microbiome*, 5:10, 16 pages (2017).

Karas et al., "A review of mortality due to Clostridium difficile infection," *J Infect.*, 61(1):1-8 (2010).

Kassam et al., "Fecal transplant via retention enema for refractory or recurrent Clostridium difficile infection," *Arch Intern Med.*, 172(2):191-193 (2012).

Kelly et al., "Commensal gut bacteria: mechanisms of immune modulation," *Trends in Immunology*, 26(6):326-333 (2005).

Kelly et al., "Clostridium difficile—more difficult than ever," *N. Engl. J. Med.*, 359(18):1932-1940 (2008).

Kelly et al., "Clostridium difficile colitis," *N. Engl. J. Med.*, 330(4):257-62 (1994).

Kelly et al., "Fecal Microbiota Transplant for Treatment of *Clostridium difficile* Infection in Immunocompromised Patients," *Am J Gastroenterol*, 109:1065-1071 (2014).

Kelly et al., "Fecal microbiota transplantation for relapsing Clostridium difficile infection in 26 patients: methodology and results," *J. Clin. Gastroenterol.*, 46(2):145-149 (2012).

Keynan et al., "The Role of Regulatory T Cells in Chronic and Acute Viral Infections," *Clinical Infectious Diseases*, 46:1046-1052 (2008).

Khanna et al., "A Novel Microbiome Therapeutic Increases Gut Microbial Diversity and Prevents Recurrent Clostridium difficile Infection," *The Journal of Infectious Diseases*, 214:173-81 (2016).

Khanna et al., "The epidemiology of community-acquired Clostridium difficile infection: a population-based study," *Am J Gastroenterol.*, 107(1):89-95 (2012).

Khanna et al., "The growing incidence and severity of Clostridium difficile infection in inpatient and outpatient settings," *Expert Rev Gastroenterol Hepatol.*, 4(4):409-16 (2010).

Kharidia et al., "The Activity of a Small Lytic Peptide PTP-7 on Staphylococcus aureus Biofilms," *J. Microbiol.*, 49(4):663-668 (2011).

Khoruts et al., "Changes in the composition of the human fecal microbiome after bacteriotherapy for recurrent Clostridium difficile-associated diarrhea," *J. Clin. Gasfroenterol.*, 44(5):354-360 (2010).

Khoruts et al., "Therapeutic transplantation of the distal gut microbiota," *Mucosal Immunol.*, 4(1):4-7 (2011).

Kim et al., "Effect of Rifampin on the Plasma Concentration and the Clinical Effect of Haloperidol Concomitantly Administered to Schizophrenic Patients," *Journal of Clinica Psychopharmacology*, 16(3):247-252 (1996).

Kim et al., "In Vitro Culture Conditions for Maintaining a Complex Population of Human Gastrointestinal Tract Microbiota," *Journal of Biomedicine and Biotechnology*, 2011(Article ID 838040):1-10 (2011) <http://www.hindawi.com/journals/bmri/2011/838040/>.

Klaenhammer, "Bacteriocins of lactic acid bacteria," *Biochimie*, 70:337-49 (1988).

Kleiman et al., "Comparison of two coprological methods for the veterinary diagnosis of fasciolosis," *Arquivo Brasileiro de Medicina Veterinária e Zootécnica*, 55(2):181-185 (2005).

Kobashi et al., "Metabolism of Sennosides by Human Intestinal Bacteria," *Journal of Medicinal Plant Research*, 40(3):225-236 (1980).

Koch, "What size should a bacterium be? A question of scale," *Annu. Rev. Microbiol.*, 50:317-48 (1996).

Krogius-Kurikka et al., "Sequence analysis of percent G+C fraction libraries of human faecal bacterial DNA reveals a high number of Antinobacteria," *BMC Microbiology*, 9(68):1-13 (2009).

Kuijper et al. "Update of Clostridium difficile Infection due to PCR Ribotype 027 in Europe, 2008," *Euro. Surveill.*, 13(31):Article 5 (2008).

Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).

Kunde et al., "Safety, Tolerability, and Clinical Response After Fecal Transplantation in Children and Young Adults With Ulcerative Colitis," *JPNG*, 56(6):597-601 (2013).

Kyne et al., "Association between antibody response to toxin A and protection against recurrent Clostridium difficile diarrhea," *Lancet*, 357(9251):189-93 (2001).

Kyne et al., "Asymptomatic carriage of Clostridium difficile and serum levels of IgG antibody against toxin A," *N Engl J Med.*, 342(6):390-397 (2000).

Kyne et al., "Factors associated with prolonged symptoms and severe disease due to Clostridium difficile," *Age and Ageing*, 28(2):107-13 (1999).

Kysela et al., "Serial analysis of V6 ribosomal sequence tags (SARST-V6): a method for efficient, high-throughput analysis of microbial community composition," *Environmental Microbiology*, 7(3):356-364 (2005).

Labbé et al., "Clostridium difficile infections in a Canadian tertiary care hospital before and during a regional epidemic associated with the BI/NAP1/027 strain," *Antimicrob Agents Chemother.*, 52(9):3180-7 (2008).

Lamontagne et al., "Impact of emergency colectomy on survival of patients with fulminant Clostridium difficile colitis during an epidemic caused by a hypervirulent strain," *Ann. Surg.*, 245(2):267-272 (2007).

Larsen et al., "Gut Microbiota in Human Adults with Type 2 Diabetes Differs from Non-Diabetic Adults," *PLoS ONE*, 5(2): e9085-e9095 (2010).

Lau et al., "Bacteraemia caused by *Anaerotruncus colihominis* and emended description of the species," *J Clin Pathol*, 59:748-752 (2006).

Lawson et al., "*Anaerotruncus colihominis* gen. nov., sp. nov., from human faeces," *International Journal of Systematic and Evoluntionary Microbiology*, 54:413-417 (2004).

Lawson et al., "Anaerotruncus," *Bergey's Manual of Systematics of Archae and Bacteria*, pp. 1-4 (2009).

Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.

Leis et al., "Fecal microbiota transplantation: A 'How-To' guide for nurses," *Collegian*, 22:445-451 (2015).

Lewis et al., "Stool form scale as a useful guide to intestinal transit time," *Scand. J. Gastroenterol.*, 32(9):920-924 (1997).

Ley et al., "Ecological and evolutionary forces shaping microbial diversity in the human intestine," *Cell*, 124:837-848 (2006).

Ley et al., "Evolution of mammals and their gut microbes," *Science*, 320(5883):1647-1651 (2008).

Ley et al., "Microbial ecology human gut microbes associated with obesity," *Nature*, 444(7122):1022-3 (2006).

Ley et al., "Worlds within worlds: evolution of the vertebrate gut microbiota," *Nat. Rev. Microbiol.*, 6(10):776-788 (2008).

Lin et al., "Twelve Week Storage Trial of Microbial Viability in Lyophilized and Frozen Fecal Microbiota Preparations," Poster Presentation—Digestive Disease Week 2015, Washington, D.C. USA.

Longstreth, "Irritable bowel syndrome: A multibillion-dollar problem," *Gastroenterology*, 109(6):2029-2031 (1995).

(56) References Cited

OTHER PUBLICATIONS

Loo et al., "A predominantly clonal multiinstitutional outbreak of Clostridium difficile-associated diarrhea with high morbidity and mortality," *N Engl J Med*, 353(23):2442-9 (2005).
Loo et al., "Host and pathogen factors for Clostridium difficile infection and colonization," *N Engl J Med*, 365(18):1693-703 (2011).
Louie et al., "Fidaxomicin versus vancomycin for Clostridium difficile infection," *N. Engl. J. Med.*, 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," *FEMS Microbiology Letters*, 294:1-8 (2009).
Lu, "Taboo transplant: How new poo defeats superbugs," Science News, 1:90-91 (2011).
Ludwig et al., "Taxonomic outline of the phylum *Firmicutes*," Bergey's Manual of Systematic Bacteriology, 3:15-17 (2009).
Lund-Tonnesen et al., "Clostridium difficile-associated diarrhea treated with homologous faeces," *Tidsskr nor Lageforen*, 118:1027-1030 (1998).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7β-Hydroxysteroid Dehydrogenase-Elaborating Eubacterium aerofaciens Strain Cocultured with 7α-Hydroxysteroid Dehydrogenase-Elaborating Organisms," *Applied and Environmental Microbiology*, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," *Can J Gastroenterol*, 15(12):817-22 (2001).
Maizels et al., "Regulatory T cells in Infection," *Advances in Immunology*, Chapter 3, 112:73-136 (2011).
Marchesi et al., "The normal intestinal microbiota," *Curr. Opin. Infect. Dis.*, 20(5):508-513 (2007).
Martin, "Development and Delivery of a Treatment for Clostridium difficile," *Bacteriotherapy*, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," *European Journal of Pharmaceutical Sciences*, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353 (23):2433-41 (2005).
McDonald et al., "Clostridium difficile Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: Clostridium difficile infections—epidemiology and current treatment strategies," *Curr Opin Gastroenterol.*, 25(1):24-35 (2008).

Miller et al., "Health care-associated Clostridium difficile infection in Canada: patient age and infecting strain type are highly predictive of severe outcome and mortality," *Clin Infect Dis.*, 50(2):194-201 (2010).
Miller et al., "Long-term follow-up of patients with fulminant Clostridium difficile colitis," *J. Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *Anaerobe*, 15(6):281-284 (2009).
Moayyedi et al., "Fecal Microbiota Transplantation Induces Remission in Patients With Active Ulcerative Colitis in a Randomized Controlled Trial," *Gastroenterology*, 149(1):102-9 (2015).
Molecular Studies in Autism, 2004 Funding Cycle, Cure Autism Now, Cure Autism Now Foundation, pp. 1-7 (2005) <www.cureautismnow.org>.
Momose et al., "16S rRNA gene sequence-based analysis of clostridia related to conversion of germfree mice to the normal state," *Journal of Applied Microbiology*, 107:2088-2097 (2009).
Morris et al., "Clostridium difficile Colitis: An Increasingly Aggressive Iatrogenic Disease?" *Arch Surg.*, 137(10):1096-1100 (2002).
Mullard, "Microbiology: The Inside Story," *Nature*, 453:578-580 (2008).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneeskd*, 152(35):1927-32 (2008) (English absract).
Niu et al., "Prevalence and Impact of Bacteriophages on the Presence of Escherichia coli O157:H7 in Feedlot Cattle and Their Environment," *Applied and Environmental Microbiology*, 75(5):1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," *Infect Control Hosp Epidemiol.*, 28(11):1219-27 (2007).
O'Connor et al., "Clostridium difficile Infection Caused by the Epidemic BI/NAP1/027 Strain," *Gastroenterology*, 136(6):1913-1924 (2009).
Office Action dated Sep. 18, 2015, in European Patent Application No. 11 728 077.6.
O'Garra et al., "IL-10—producing and naturally occuring CD4+ Tregs: limiting collateral damage," *The Journal of Clinical Investigation*, 114:1372-1378 (2004).
Okada et al., "Effects of Fecal Microorganisms and Their Chloroform-Resistant Variants Derived from Mice, Rats, and Humans on Immunological and Physiological Characteristics of the Intestines of Ex-germfree Mice," *Infection and Immunity*, 62(12):5442-5446 (1994).
Ott et al., "Efficacy of Sterile Fecal Filtrate Transfer for Treating Patients With Clostridium difficile Infection," *Gastroenterology*, 152(4):799-811 (2017).
Paramsothy et al., "Gastroenterologist perceptions of faecal microbiota transplantation," *World J Gastroenterol*, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).

(56) References Cited

OTHER PUBLICATIONS

Patterson et al., "Special organism isolation: attempting to bridge the gap," *Infect Control Hosp Epidemiol.*, 15(5):335-338 (1994).
Pearce et al., "Modification of the colonic microflora using probiotics: The way forward?," *Gut*, 41(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pépin et al., "Clostridium difficile-associated diarrhea in a region of Quebec from 1991 to 2003: a changing pattern of disease severity," *CMAJ*, 171(5):466-472 (2004).
Pépin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).
Pépin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al.,"Stool substitute transplant therapy for the eradication of Clostridium difficile infection: 'RePOOPulating' the gut," *Microbiome*, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), Remington: The Science and Practice of Pharmacy, Chapter 46, pp. 929-938 (2005).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson MICROMEDEX, pp. 1-4, n.d., Web, Nov. 23, 2005.
Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J. Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rea et al., "Gut solutions to a gut problem: bacteriocins, probiotics and bacteriophage for control of Clostridium difficile infection," *Journal of Medical Microbiology*, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11 728 077.6.
Response to Office Action filed Jan. 28, 2015, in European Patent Application No. 11 728 077.6.
Response to Office Action filed Nov. 18, 2015, in European Patent Application No. 11 728 077.6.

Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent Clostridium difficile infection: results and methodology," *J Clin Gastroenterol.*, 44(8):567-570 (2010).
Rolfe et al., "Bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," *Gastroenterology*, 149(1):110-8 (2015).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *Nat. Rev. Microbiol.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J. Infect. Dis.*, 186(12):1781-1789 (2002).
Sanchez et al., "The Role of Natural Regulatory T cells in Infection," *Immunol Res.*, 49(0):124-134 (2011).
Sandler et al., "Possible Gut-Brain Interaction Contributing to Delayed Onset Autism Symptomatology," *Fourth Int. Symp. Brain-Gut Interactions*, Blackwell Science Ltd., 10(4):33 (1998).
Sandler et al., "Short-Term Benefit From Oral Vancomycin Treatment of Regressive-Onset Autism," *Journal of Child Neurology*, 15(7):429-435 (2000).
Sartor, "Therapeutic correction of bacterial dysbiosis discovered by molecular techniques," *PNAS*, 105(43):16413-16414 (2008).
Schiller, "Review article, the therapy of constipation," *Ailment Pharmacol. Ther.*, 15:749-763 (2001).
Schloss, "Introducing mothur: Open-Source, Platform-Independent, Community-Supported Software for Describing and Comparing Microbial Communities," *Appl. Environ. Microbiol.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J. Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Setlow, "I Will Survive: Protecting and Repairing Spore DNA," *Journal of Bacteriology*, 174(9):2737-2741 (1992).
Setlow, "The bacterial spore: nature's survival package," *Culture*, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shim et al., "Primary symptomless colonisation by Clostridium difficile and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).

(56) References Cited

OTHER PUBLICATIONS

Singh et al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," *Gastroenterology*, 145:946-953 (2013).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Inflamm. Bowel Dis.*, pp. 1-7 (2009).
Sunil et al., "Design and evaluation of lornoxicam bilayered tablets for biphasic release," *Brazilian Journal of Pharmaceutical Sciences*, 48(4):609-19 (2012).
Surawicz et al., "Treatment of refractory and recurrent Clostridium difficile infection," *Nat. Rev. Gastroenterol. Hepatol.*, 8(6):330-339 (2011).
Surawicz, "Reining in Recurrent Clostridium difficile Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," *Biochim Biophys Acta*, 962(1):116-121 (1988).
Takaishi et al., "Imbalance in intestinal microflora constitution could be involved in the pathogenesis of inflammatory bowel disease," *J. Med. Microbiol.*, 298:463-472 (2008).
Takeda et al., "Serum Haloperidol Levels of Schizophrenics Receiving Treatment for Tuberculosis," *Clinical Neuropharmacology*, 9(4):386-397 (1986).
Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).
Taras et al., "Reclassification of Eubacterium formicigenerans Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tilg et al., "Gut microbiome, obesity, and metabolic dysfunction," *J. Clin. Invest.*, 121(6):2126-2132 (2011).
Tvede et al., "Bacteriotherapy for chronic relapsing Clostridium difficile diarrhea in six patients," *The Lancet*, 1:1156-1160 (1989).
Van Andel et al., "Interleukin-12 Has a Role in Mediating Resistance of Murine Strains to Tyzzer's Disease," *Infect. Immun.*, 66(10):4942-4946 (1998).
van der Waaij et al., "Direct Flow Cytometry of Anaerobic Bacteria in Human Feces," *Cytometry*, 16:270-279 (1994).
Van Immerseel et al., "Butyric acid-producing anaerobic bacteria as a novel probiotic treatment approach for inflammatory bowel disease," *Journal of Medical Microbiology*, 59:141-143 (2010).
van Nood et al., "Struggling with Recurrent Clostridium difficile Infections: Is Donor Faeces the Solution?," *Euro Surveill.*, 14(34):1-6 (2009).
van Nood, "Duodenal infusion of donor feces for recurrent Clostridium difficile," *New England Journal of Medicine*, 368(5):407-415 (2013).
Veldhuyzen van Zanten et al., "Drug Treatment of Functional Dyspepsia: A Systematic Analysis of Trial Methodology with Recommendations for Design of Future Trials," *Am. J. Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: A Novel Macrocyclic Antibiotic Approved for Treatment of Clostridium difficile Infection," *Clin Infect Dis*, 54(4):568-74 (2012).
Vrieze et al., "The environment within: how gut microbiota may influence metabolism and body composition," *Diabetologia*, 53(4):606-613 (2010).
Vulevic et al., "Modulation of the fecal microflora profile and immune function by a novel trans-galactooligosaccharide mixture (B-GOS) in healthy elderly volunteers," *Am J Clin Nutr*, 88:1438-46 (2008).
Wachsmann et al., "Characterization of an Orotic Acid Fermenting Bacterium, *Zymobacterium oroticum*, nov. gen., nov. spec.," *Journal of Bacteriology*, 68(4):400-404 (1954).
Walter et al., "Host-microbial symbiosis in the vertebrate gastrointestinal tract and the Lactobacillus reuteri paradigm," *PNAS USA*, 108(Suppl 1):4645-4652 (2011).
Warny et al., "Toxin production by an emerging strain of Clostridium difficile associated with outbreaks of severe disease in North America and Europe," *Lancet*, 366(9491):1079-84 (2005).
Warren et al., "*Clostridium aldenense* sp. nov. and *Clostridium citroniae* sp. nov. Isolated from Human Clinical Infections," *Journal of Clinical Microbiology*, 44(7):2416-2422 (2006).
Wasfy et al., "Comparison of Preservation Media for Storage of Stool Samples," *Journal of Clinical Microbiology*, 33(8):2176-2178 (1995).
Weingarden et al., "Dynamic changes in short- and long-term bacterial composition following fecal microbiota transplantation for recurrent Clostridium difficile infection," *Microbiome*, 3(10), 8 pages (2015).
Weissman et al., "Stool Transplants: Ready for Prime Time?," *Current Gastroenterology Reports*, 14:313-316 (2012).
Wells et al., "Clostridia: Sporeforming Anaerobic Bacilli," *Medical Microbiology—NCBI Bookshelf*, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—An effective Treatment for Relapsing Symptomatic Clostridium difficile Infection," *Abstract, 15th United European Gastroenterology Week (UEGW) Poster presentations, United European Gastroenterology Federation, France*, A303 (2007).
Wettstein et al., "Skewered diverticulum: another cause of abdominal pain," *Internal Med J*, 31(8):495-496 (2001).
Wikoff et al., "Metabolomics analysis reveals large effects of gut microflora on mammalian blood metabolites," *PNAS*, 106(10):3698-3703 (2009).
Wilson et al., "Human Colonic Biota Studied by Ribosomal DNA Sequence Analysis," *Appl. Environ. Microbiol.*, 62(7):2273-2278 (1996).
Yoon et al., "Treatment of Refractory/Recurrent C. difficile-associated Disease by Donated Stool Transplanted Via Colonoscopy: A Case Series of 12 patients," *J Clin Gastroenterol.*, 44(8):562-566 (2010).
You et al., "Successful treatment of fulminant Clostridium difficile infection with fecal bacteriotherapy," *Ann. Intern. Med.*, 148(8):632-633 (2008).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zhou et al., "Total fecal microbiota transplantation alleviates high-fat diet-induced steatohepatitis in mice via beneficial regulation of gut microbiota," *Scientific Reports (Nature)*, 7(1529):1-11 (2017).
Jergens et al., "Induction of differential immune reactivity to members of the flora of gnotobiotic mice following colonization with *Helicobacter bilis* or *Brachyspira hyodysenteriae*," *Microbes and Infection*; 8:1602-1610 (2006).
Jergens, "Resident enteric flora modulates the development of colitis in gnotobiotic mice," *Retrospective Theses and Dissertations*, 1824:1-116 (2005).

(56) References Cited

OTHER PUBLICATIONS

Synthetic, (n.d.), Dictionary.com, The American Heritage® Science Dictionary, pp. 1-3, retrieved: May 14, 2018 <http://www.dictionary.com/browse/syntheitic>.

* cited by examiner

METHODS FOR TREATING ULCERATIVE COLITIS

CROSS-REFERENCE TO RELATED APPLICATIONS

This application is a U.S. Non-Provisional application which is a continuation of International Application No. PCT/US2017/045092 filed Aug. 2, 2017, which claims the benefit of U.S. Provisional Application No. 62/370,508 filed Aug. 3, 2016, which is incorporated by reference in its entirety herein.

FIELD

The present disclosure relates to methods and dosing regimens suitable for treating ulcerative colitis in a subject in need thereof.

BACKGROUND

Mammals harbor diverse microbial species in their gastrointestinal (GI) tracts. Interactions between these microbes and between microbes and the host, e.g. the host immune system, shape a microbiota. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. An unbalanced microbiota (also called 'dysbiosis' or disrupted symbiosis) may lose its function and results in increased susceptibility to pathogens, altered metabolic profiles, or induction of proinflammatory signals that can lead to local or systemic inflammation or autoimmunity. The intestinal microbiota plays a significant role in the pathogenesis of many disorders such as pathogenic infections of the gut.

Ulcerative colitis is a chronic disease of the large intestine, also known as the colon, in which the lining of the colon becomes inflamed and develops tiny open sores, or ulcers, that produce pus and mucous. Ulcerative colitis occurs most often in people ages 15 to 30, although the disease may afflict people of any age. It affects men and women equally and appears to run in some families.

Ulcerative colitis is a disease that is characterized by inflammation and micro-ulcers in the superficial layers of the large intestine. The inflammation usually occurs in the rectum and lower part of the colon, but it may affect the entire large intestine (pancolitis). Ulcerative colitis can very rarely affect the small intestine in its distal portion (Backwash Ileitis).

The inflammation is accompanied usually with diarrhea, which may be profuse and bloody. Micro-ulcers form in places where inflammation has destroyed the cells lining the bowel and these areas bleed and produce pus and mucus. Ulcerative colitis, especially when mild, can be difficult to diagnose because symptoms are similar to other intestinal disorders, most notably the other type of Irritable Bowel Diseases (IBD) called Crohn's disease and also irritable bowel syndrome. Crohn's disease differs from ulcerative colitis because it causes inflammation throughout the whole thickness of the intestinal wall and produces deep ulcers. Crohn's disease usually occurs in the small intestine, but it can also occur in the large intestine, anus, esophagus, stomach, appendix and mouth. Crohn's disease causes fistulae whereas ulcerative colitis does not. Both Crohn's and ulcerative colitis may co-exist in the same patient. The combination of inflammation and ulceration can cause abdominal discomfort and frequent emptying of the colon. Existing treatments for ulcerative colitis involve intense and lengthy combinational drug therapy with significant side effects or even require surgery to remove part of the colon. Moreover, a substantial proportion of ulcerative colitis patients are resistant to standard drug therapy. Thus, there is a need for more effective treatments for ulcerative colitis that are easier to administer.

Implantation or administration of human colonic microbiota into the bowel of a sick patient is called Fecal Microbiota Transplantation (FMT), also commonly known as fecal bacteriotherapy. FMT is believed to repopulate the gut with a diverse array of microbes that control key pathogens by creating an ecological environment inimical to their proliferation and survival. It represents a therapeutic protocol that allows a fast reconstitution of a normal compositional and functional gut microbial community.

Fecal microbiota transplantation (FMT), also known as 'fecal bacteriotherapy,' represents the one therapeutic protocol that allows the fastest reconstitution of a normal composition and functional gut microbial community. For many decades, FMT has been offered by select centers across the world, typically as an option of last resort for patients with recurrent *Clostridium difficile* infection (CDI). FMT has also been suggested in treating other gut infective agents such as *E. coli* and Vancomycin resistant Enterococci (VRE). Currently, FMT is administered by several routes including infusion of human microbiota in the form of homogenized stool, extracts of homogenized stool, or cultured stool components through a colonoscope, an enema, or via a nasojejunal tube.

SUMMARY

The present disclosure provides methods and dosing regimens for treating or preventing ulcerative colitis.

In one aspect, the present disclosure provides a method for treating ulcerative colitis in a subject in need thereof, where the method comprises treating said patient with a treatment regimen comprising the administration of a pharmaceutical composition comprising live non-pathogenic fecal bacteria for at least 8 weeks and at least three times per week.

In an aspect, this disclosure provides a method for treating ulcerative colitis (UC) in a subject in need thereof and exhibiting a Mayo endoscopy score of 3 or lower, where the method comprises administering to said subject a pharmaceutical composition comprising live non-pathogenic fecal bacteria.

In an aspect, the present disclosure provides a method for treating ulcerative colitis in a subject in need thereof, where the method comprises administering to the subject a pharmaceutical composition comprising live non-pathogenic fecal bacteria, where the subject has no concomitant corticosteroid use during the method and has no corticosteroid use immediately prior to commencing the method.

In one aspect, the present disclosure provides a method for selecting a treatment plan for treating ulcerative colitis (UC) in a subject in need thereof, where the method comprises determining the level of *Fusobacterium, Sutterella*, or both in said subject's gut; and recommending a fecal bacteria-based therapy when said level of *Fusobacterium, Sutterella*, or both is above a predetermined level.

In an aspect, the present disclosure provide as method for selecting a treatment plan for treating ulcerative colitis (UC) in a subject in need thereof, where the method comprises determining the level of one or more bacteria selected from the group consisting of *Barnesiella, Parabacteroides, Clostridium* IV, *Ruminococcus, Blautia, Dorea, Ruminococcus*2, and *Clostridium* XVIII in said subject's gut; and recommending a fecal bacteria-based therapy when said level of one or more bacteria selected from the group consisting of is above a predetermined level.

DETAILED DESCRIPTION

Figure 1:
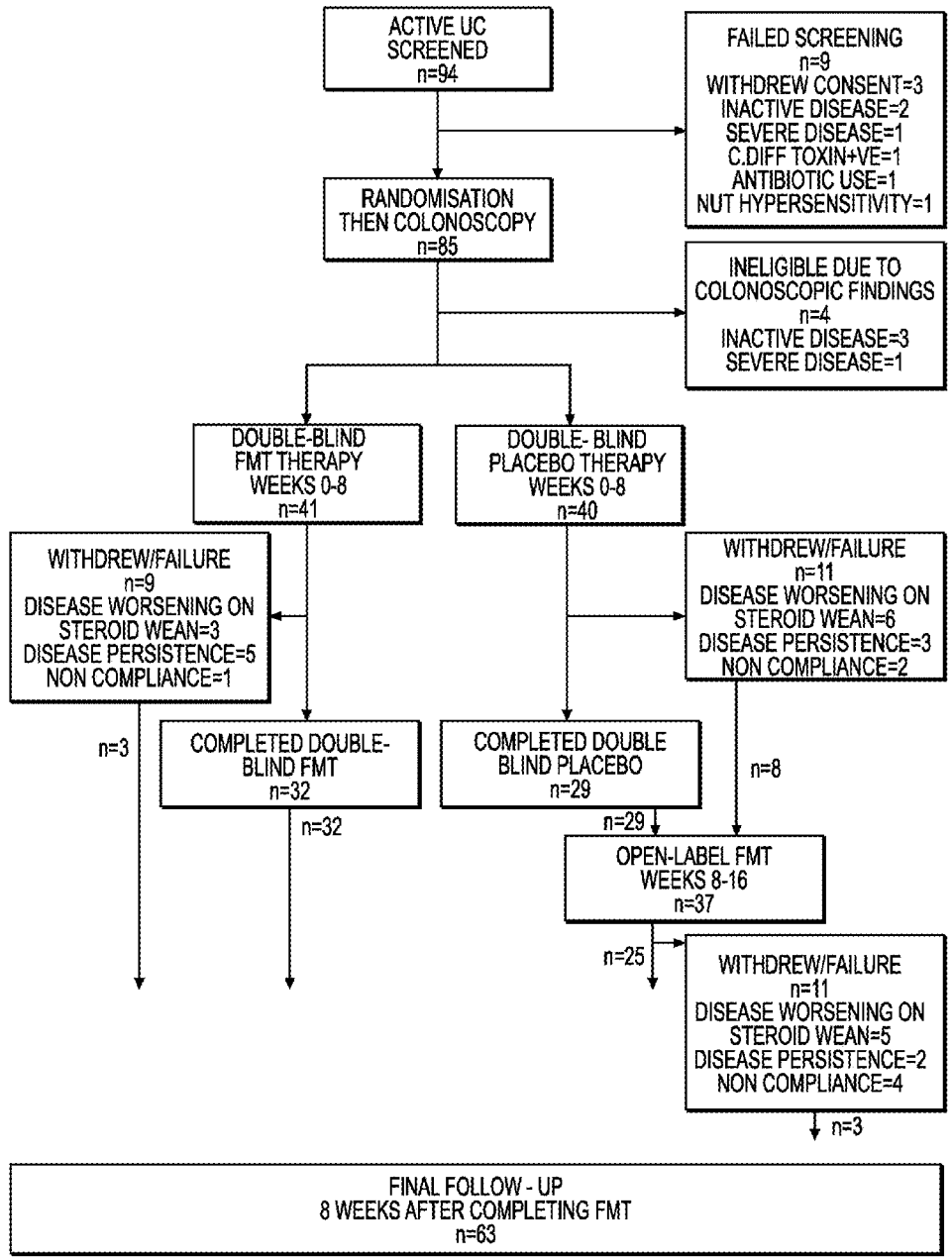
FIG. 1 shows a study patient CONSORT Flow Diagram in accordance with Example 1 of the present disclosure.

Before the present compositions and methods are described, it is to be understood that the present disclosure is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations and variations thereof.

Unless defined otherwise herein, terms are to be understood according to conventional usage by those of ordinary skill in the relevant art. The terminology used in the description of the disclosure herein is for the purpose of describing particular embodiments only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentages, density, volume and the like, is meant to encompass variations of 20%, 10%, 5%, 1%, 0.5%, or even 0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "substantially free" as used herein when referring to a substance's presence in a composition, is meant to encompass that the substance constitutes less than 1%, less than 0.5%, less than 0.1%, or even less than 0.01% of the whole substance by volume or mass.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

As used herein, "microbiota," and "flora" refer to a community of microbes that live in or on a subject's body, both sustainably and transiently, including eukaryotes, archaea, bacteria, and viruses (including bacterial viruses (i.e., phage)). A non-selective fecal microbiota refers to a community or mixture of fecal microbes derived from a donor's fecal sample without selection and substantially resembling microbial constituents and population structures found in such fecal sample.

As used herein, "remission," "cure," or "resolution rate" refers to the percentage of patients that are cured or obtain remission or complete resolution of a condition in response to a given treatment. As used herein, "clinical remission sustaining rate" refers to the percentage of patients remaining in clinical remission after a specified post-treatment period among all patients who achieve remission at the completion of a treatment. Quantitatively, remission, cure, or resolution is achieved when a patient's UCDAI score is below or equal to 2, assessed after 8 weeks of treatment. Remission, cure, or resolution can be further confirmed by endoscopic and mucosal healing.

As used herein "steroid-free" refers to a complete lack or a substantial lack of steroid use.

As used herein, "primary outcome rate" refers to the percentage of patients achieving primary outcome after a specific treatment or treatment regimen among all patients receiving that treatment or treatment regimen.

As used herein, "response rate" refers to the percentage of patients that respond positively to a given treatment. Quantitatively, a patient responds to a treatment positively when the patient's UCDAI score decreases by at least 2 from baseline to week 8.

As used herein, "Mayo Clinic score" or "Mayo score" refers to an index system for assessing the severity of a ulcerative colitis disease condition. See Table 1 and Schoeder et al. N Engl J Med 1987; 317:1625-9. The Mayo Clinic score ranges from 0-12, with sub-scores of 0-3, where the higher scores indicate more severe disease. In some aspects, sub-scores may be rated for stool frequency, rectal bleeding, mucosal appearance at endoscopy, and physician's global assessment (PGA).

TABLE 1

Mayo Clinic Scoring System for Assessment of Ulcerative Colitis Activity (Shoeder et al.)

| | score assignment |
|---|---|
| 1. Stool frequency* | |
| Normal number of stools for this patient | 0 |
| 1-2 stools more than normal | 1 |
| 3-4 stools more than normal | 2 |
| 5 or more stools more than normal | 3 |
| 2. Rectal Bleeding† | |
| No blood seen | 0 |
| Streaks of blood with stool less half the time | 1 |
| Obvious blood with stool most of the time | 2 |
| Blood alone passed | 3 |
| 3. Findings of flexible proctosigmoidoscopy | |
| Normal or inactive disease | 0 |
| Mild disease (erythema, decreased vascular pattern, mild friability) | 1 |
| Moderate disease (marked erythema, absent vascular pattern, friability, erosions) | 2 |
| Severe disease (spontaneous bleeding, ulceration) | 3 |
| 4. Physician's global assessment‡ | |
| Normal | 0 |
| Mild disease | 1 |
| Moderate disease | 2 |
| Severe disease | 3 |

*Each patient served as his or her own control to establish the degree of abnormality of the stool frequency
†The daily bleeding score represented the most severe bleeding of the day
‡The physician's global assessment acknowledged the three other criteria, the patient's daily record of abdominal discomfort and general sense of well-being, and other observations, such as physical findings and the patient's performance status As used herein, "ulcerative colitis endoscopic index of severity" or "UCEIS" refers to an index for assessing endoscopic disease activity. The index assesses three criteria, including vascular pattern, bleeding, and erosions and ulcers (Table 2). See Travis et al., Developing an instrument to assess the endoscopic severity of ulcerative colitis: the Ulcerative Colitis Endoscopic Index of Severity (UCEIS), *Gut* 2012, 61(4):535-42. A higher score reflects increased disease severity.

TABLE 2

Scoring System for Ulcerative Colitis Endoscopic Index of Severity (See Travis et al.)

| | score assignment |
|---|---|
| 1. Vascular pattern | |
| Normal: Normal vascular pattern with arborization of capillaries clearly defined, or with blurring or patchy loss of capillary margins | 1 |
| Patchy obliteration: Patchy obliteration of vascular pattern | 2 |
| Obliterated: Complete obliteration of vascular pattern | 3 |
| 2. Rectal bleeding | |
| None: No visible blood | 1 |
| Mucosal: Some spots or streaks of coagulated blood on the surface of the mucosa ahead of the scope, which can be washed away | 2 |
| Luminal mild: Some free liquid blood in the lumen | 3 |
| Luminal moderate or severe: Frank blood in the lumen ahead of endoscope or visible oozing from mucosa after washing intra-luminal blood, or visible oozing from a hemorrhagic mucosa | 4 |

TABLE 2-continued

Scoring System for Ulcerative Colitis Endoscopic
Index of Severity (See Travis et al.)

| | score assignment |
|---|---|
| 3. Erosions and ulcers | |
| None: Normal mucosa, nonvisible erosions or ulcers | 1 |
| Erosions: Tiny (≥5 mm) defects in the mucosa, of a white or yellow color with a flat edge | 2 |
| Superficial ulcer: Larger (>5 mm) defects in the mucosa, which are discrete fibrin-covered ulcers when compared to erosions, but remain superficial | 3 |
| Deep ulcer: Deeper excavated defects in the mucosa, with a slightly raised edge | 4 |

As used herein, "ulcerative colitis disease activity index" or "UCDAI" refers to an index system for assessing the symptomatic severity or response of a ulcerative colitis patient. The index assesses four variables, which include stool frequency, severity of bleeding, colonic mucosal appearance, and the physician's overall assessment of disease activity (Table 3). See Sutherland et al., 5-Aminosalicylic acid enema in the treatment of distal ulcerative colitis, proctosigmoiditis, and proctitis. *Gastroenterology.* 1987; 92:1894-8. Each variable is scored from 0-3 so that the total index score ranges from 0-12; 0-2: remission; 3-6: mild; 7-10: moderate; >10: severe ulcerative colitis.

TABLE 3

Scoring System for Ulcerative Colitis Disease
Activity Index. (See Tursi et al.)

| | score assignment |
|---|---|
| 1. Stool frequency | |
| Normal | 0 |
| 1-2 Stools/day > normal | 1 |
| 3-4 Stools/day > normal | 2 |
| >4 Stools/day > normal | 3 |
| 2. Rectal bleeding | |
| None | 0 |
| Streaks of blood | 1 |
| Obvious blood | 2 |
| Mostly blood | 3 |
| 3. Mucosal appearance | |
| Normal | 0 |
| Mild friability | 1 |
| Moderate friability | 2 |
| Exudation, spontaneous bleeding | 3 |
| 4. Physician's rating of disease activity | |
| Normal | 0 |
| Mild | 1 |
| Moderate | 2 |
| Severe | 3 |

As used herein, "eukaryotic" refers to belonging to a cell that contains a nucleus and membrane-bound organelles.

As used herein, "bacteria," "bacterium," and "archaea" refer to single-celled prokaryotes that lack membrane bound nuclei and lack organelles.

As used herein, "fecal bacteria" refers to bacteria that can be found in fecal matter.

As used herein, "viable" means possessing the ability to multiply.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $$H = -\sum_{i=1}^{R} p_i \ln p_i$$

where H is the Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication.* The University of Illinois Press, Urbana. 117 pp.

As used herein, "operational taxonomic unit" or "OTU" refers to a group of closely related microbial species determined based on 16S or 18S rRNA marker genes.

As used herein, "antibiotic" refers to a substance that is used to treat and/or prevent bacterial infection by killing bacteria, inhibiting the growth of bacteria, or reducing the viability of bacteria.

As used herein, an "intermittent dosing schedule" means that a therapeutic composition is administered for a period of time followed by a period of time (a treatment period) where treatment with such therapeutic composition is withheld (a rest period). Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day.

As used herein, a "continuous dosing schedule" refers to a dosing schedule where a therapeutic composition is administered during a treatment period without a rest period. Throughout the treatment period of a continuous dosing schedule, a therapeutic composition can be administered, for example, daily, or every other day, or every third day. On a day when a therapeutic composition is administered, it can be administered in a single dose, or in multiple doses throughout the day.

As used herein, "dosing frequency" refers to the frequency of administering doses of a therapeutic composition in a given time. Dosing frequency can be indicated as the number of doses per a given time, for example, once per day, once a week, or once in two weeks.

As used herein, "dosing interval" refers to the amount of time that elapses between multiple doses being administered to a subject.

Different types of ulcerative colitis exist. As used herein, "ulcerative proctitis" refers to a disease form where bowel inflammation is limited to the rectum. Because of its limited extent (usually less than the six inches of the rectum), ulcerative proctitis tends to be a milder form of ulcerative colitis. It is associated with fewer complications and offers a better outlook than more widespread disease. For approximately 30% of all patients with ulcerative colitis, the illness begins as ulcerative proctitis.

As used herein, "proctosigmoiditis" refers to a form of colitis affecting the rectum and the sigmoid colon, the lower segment of colon located right above the rectum. Symptoms include bloody diarrhea, cramps, and a constant feeling of the need to pass stool, known as tenesmus. Moderate pain on the lower left side of the abdomen may occur in active disease.

As used herein, "left-sided colitis" refers to continuous inflammation that begins at the rectum and extends as far as a bend in the colon near the spleen called the splenic flexure. Symptoms include loss of appetite, weight loss, diarrhea, severe pain on the left side of the abdomen, and bleeding.

As used herein, "pan-ulcerative (total) colitis" affects the entire colon. Symptoms include diarrhea, severe abdominal pain, cramps, and extensive weight loss. Potentially serious complications include massive bleeding and acute dilation of the colon (toxic megacolon), which may lead to an opening in the bowel wall. Serious complications may require surgery.

Several theories have been proposed for the cause of ulcerative colitis. There is some evidence to suggest that the body's immune system reacts to an environmental, dietary or infectious agent in genetically susceptible individuals causing inflammation in the intestinal wall. The latest postulated causal agent is the to be an infection of the lining with a *Fusobacterium varium* identified by researchers from Japan. Ulcerative colitis is not caused by emotional distress or sensitivity to certain foods or food products but these factors may trigger symptoms in some people. Ulcerative colitis is most likely not an aberrant reaction but an infection.

The most common symptoms of ulcerative colitis are bloody diarrhea and abdominal pain. Patients also may experience fever, rectal bleeding, fatigue, anaemia, loss of appetite, weight loss and loss of body fluids and nutrients resulting in nutritional deficiencies. These symptoms occur as intermittent attacks in between periods when the symptoms go away (remissions). These disease-free periods can last for months or even years. Usually an attack begins with increased urgency to defecate, mild lower abdominal cramps, and blood and mucus in the stools.

Ulcerative colitis may cause long-term problems such as arthritis, inflammation of the eye, liver disease (fatty liver, hepatitis, cirrhosis, and primary sclerosing cholangitis), osteoporosis, skin rashes, anaemia and kidney stones. These complications may occur when the immune system triggers inflammation in other parts of the body. These problems can disappear when the colitis is treated effectively.

Treatment for ulcerative colitis depends on the seriousness of the disease. Most people are treated with medication. Some people whose symptoms are triggered by certain foods are able to control the symptoms by avoiding foods that upset their intestines, like highly seasoned foods or dairy products. Each person may experience ulcerative colitis differently, so treatment is adjusted for each individual.

Many patients with mild or moderate disease are first treated with 5-ASA agents, including a combination of the drugs 5-aminosalicylic acids and sulfasalazine that helps control inflammation. Sulfasalazine is the most commonly used of these drugs. Sulfasalazine can be used for as long as needed and can be given along with other drugs. Patients who do not do well on sulfasalazine may respond to newer 5-ASA agents. Possible side effects of 5-ASA preparations include nausea, vomiting, heartburn, diarrhea and headache.

People with severe disease and those who do not respond to 5-ASA preparations may be treated with added corticosteroids. Prednisone and budesonide and hydrocortisone are corticosteroids used to reduce inflammation. They can be given orally, intravenously, through an enema, or in a suppository, depending on the location of the inflammation. Corticosteroids can cause side effects such as weight gain, acne, facial hair, hypertension, diabetes, mood swings, and increased risk of infection, so doctors carefully monitor patients taking these medications.

Immunosuppressants such as azathioprine, 6-mercaptopurine (6-MP) and methotrexate are often used and can make a marked improvement at a low dose with few side effects. Other drugs may be given to relax the patient or to relieve pain, diarrhea, or infection. Occasionally, symptoms are severe enough that the person must be hospitalized. For example, a person may have severe bleeding or severe diarrhea that causes dehydration. In such cases the doctor will try to stop diarrhea and loss of blood, fluids, and mineral salts. The patient may need a special diet, feeding through a vein, medications, or sometimes surgery.

In severe cases, a patient may need surgery to remove the diseased colon. Sometimes the doctor will recommend removing the colon if medical treatment fails or if the side effects of corticosteroids or other drugs threaten the patient's health.

In one aspect, the present disclosure provides a method for reducing the level of calprotectin in a subject in need thereof, where the method comprises treating said patient with a treatment regimen comprising the administration of a pharmaceutical composition comprising live non-pathogenic fecal bacteria for at least 8 weeks and at least three times per week. In another aspect, any method or treatment regimen provided here can also be used to reduce the level of calprotectin and inflammation in a subject in need thereof. In an aspect, the present disclosure provides a method for reducing the level of calprotectin in a subject in need thereof by at least 10% compared to the calprotectin level prior to treatment. In another aspect, the level of calprotectin is reduced by at least 20%, 25%, 30%, 35%, 40%, 45%, 50%, 55%, 60%, 65%, 70%, 75%, 80%, 85%, 90%, or 95%. In another aspect, the level of calprotectin is reduced by between 2 and 10%, 10 and 20%, 20 and 30%, 30 and 40%, 40 and 50%, 50 and 60%, 60 and 70%, 70 and 80%, 80 and 85%, 85 and 90%, 90 and 95%, and 95 and 99% compared to the calprotectin level prior to treatment. In a further aspect, the level of calprotectin is reduced to below 100 µg/g, below 90 µg/g, below 80 µg/g, below 70 µg/g, below 60 µg/g, below 65 µg/g, below 55 µg/g, below 50 µg/g, below 45 µg/g, below 40 µg/g, or below 35 µg/g. In another aspect, the level of calprotectin is reduced in a subject in need thereof following a treatment regimen lasting for at least 8 weeks. In another aspect, the level of calprotectin is reduced in a subject in need thereof at 8 weeks after the completion of the treatment regimen. In yet another aspect, the level of calprotectin is reduced in a subject in need thereof between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks after the completion of the treatment regimen. In a further aspect, the level of calprotectin is reduced in a subject in need thereof between 12 and 30 weeks, between 12 and 28 weeks, between 12 and 20 weeks, between 14 and 20 weeks, between 14 and 26 weeks, between 12 and 18 weeks, between 12 and 16 weeks, between 20 and 30 weeks, between 25 and 30 weeks, and between 21 and 27 weeks after the completion of the treatment regimen. In another aspect, the level of calprotectin is reduced in a subject in need thereof after 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 18 or more, 20 or more, 22 or more, 24 or more, 26 or more, 28 or more, 30 or more, 40 or more, 50 or more weeks after the completion of the treatment regimen.

In one aspect, the present disclosure provides a method for treating ulcerative colitis in a subject in need thereof, where the method comprises treating said patient with a treatment regimen comprising the administration of a pharmaceutical composition comprising live non-pathogenic fecal bacteria for at least 8 weeks and at least three times per week. In another aspect, any method or treatment regimen provided here can also be used to treat one or more indications selected from the group consisting of collagenous colitis, lymphocytic colitis, Crohn's colitis, diverticulitis, and pouchitis.

In an aspect, this disclosure provides a method for treating ulcerative colitis in a subject in need thereof and exhibiting a Mayo endoscopy score of 3 or lower, where the method comprises administering to said subject a pharmaceutical composition comprising live non-pathogenic fecal bacteria. In one aspect, this administering is following a treatment regimen lasting for at least 8 weeks. In an aspect, this administering is following a treatment regimen of at least 8 weeks and at least three time per week. In one aspect, this administering is following a treatment regimen of at least 8 weeks and at least three times per week.

In an aspect, the present disclosure provides a method for treating ulcerative colitis in a subject in need thereof, where the method comprises administering to the subject a pharmaceutical composition comprising live non-pathogenic fecal bacteria, where the subject has no concomitant corticosteroid use during the method and has no corticosteroid use immediately prior to commencing the method. In one aspect, this administering is following a regimen lasting for at least 9 weeks. In an aspect, this administering is following a regimen of at least 8 weeks and at least three times per week.

In an aspect, the subject of the present disclosure exhibits a Mayo score of at least 4 prior to treatment, such as a Mayo score of 4, 5, 6, 7, 8, 9, 10. In one aspect, the subject of the present disclosure exhibits a Mayo score of 4 to 10 prior to treatment, such as 4 to 9, 5 to 10, 5 to 8, or 6 to 8.

In an aspect, the subject of the present disclosure exhibits an UCEIS score of at least 4 prior to treatment, such as an UCEIS score of 4, 5, 6, 7, 8, 9, 10. In one aspect, the subject of the present disclosure exhibits a UCEIS score of 4 to 10 prior to treatment, such as 4 to 9, 5 to 10, 5 to 8, or 6 to 8.

In one aspect, the subject of the present disclosure is capable of achieving a primary outcome at the end of a treatment regimen, where the primary outcome is defined as a steroid-free clinical remission and endoscopic remission or response at the end of the treatment regimen, where the steroid free clinical remission is defined as a total Mayo score of 2 or lower with sub-scores of 1 or lower, and where the endoscopic remission or response is defined as a reduction of at least 1 point from baseline in endoscopy score. In another aspect, the subject of the present disclosure is capable of achieving a primary outcome at the end of a treatment regimen, where the primary outcome is defined as a steroid-free clinical remission which is defined as a total Mayo score of 2 or lower with sub-scores of 1 or lower. In a further aspect, the subject of the present disclosure is capable of achieving a primary outcome at the end of a treatment regimen, where the primary outcome is defined as a steroid-free endoscopic remission or response which is defined as a reduction of at least 1 point from baseline in endoscopy score.

In an aspect, a subject of the present disclosure has no steroid use within at least one week prior to commencing the methods provided herein. In another aspect, a subject of the present disclosure has no steroid use within at least two, three, four, or five weeks prior to commencing the methods provided herein. In a further aspect, a subject of the present disclosure has no steroid use within at least 1, 2, 3, 4, 5, 6, 7, 8, 9, 10, 11, 12, 13, or 14 days prior to commencing the methods provided herein. In one aspect, a steroid may be prednisone, budesonide, or hydrocortisone. In an aspect, a subject of the present disclosure has no corticosteroid use within at least one week prior to commencing the methods provided herein. In one aspect, a subject of the present disclosure has no corticosteroid use prior to commencing the methods provided herein.

In some aspects, the methods of the present disclosure further comprise determining the subject's baseline gut bacterial diversity. In an aspect, a subject's baseline gut bacterial diversity is assessed by analyzing Shannon's diversity of the subject's fecal sample prior to the treating step. In one aspect, a subject's baseline fecal Shannon diversity is between 0.5 and 2.2 based on bacterial species level, such as between 0.5 and 2.0, between 1.0 and 2.2, or between 1.0 and 1.5. In an aspect, a subject's fecal Shannon diversity increases by at least 50%, 60%, 70%, 80%, 90%, 95%, 98%, 99%, 99.5%, 99.8%, or 99.9% compared to before treatment. In one aspect, a subject's fecal Shannon diversity increases by at least 1, 2, 3, 4, 5, 6, 7, 8, 9, 10, 11, 15, 20, or 30 folds compared to before treatment. In one aspect, a subject's post-treatment fecal Shannon diversity is between 1.5 and 6.0 based on bacterial species level, such as between 1.5 and 5.0, between 1.5 and 4.5, between 1.5 and 4.0, between 1.5 and 3.5, between 1.5 and 3.0, between 1.5 and 2.5, between 1.5 and 2.0, between 2.0 and 4.5, between 2.5 and 4.0, between 3.0 and 3.5, between 2.0 and 6.0, between 2.5 and 6.0, between 3.0 and 6.0, between 3.5 and 6.0, between 4.0 and 6.0, between 4.5 and 6.0, between 5.0 and 6.0, and between 5.5 and 6.0.

In certain aspects, the methods of the present disclosure further comprise determining the level of *Fusobacterium, Sutterella*, or both in a subject's gut. In some aspects, methods of the present disclosure further comprise determining the level of one or more bacteria selected from the group consisting of *Barnesiella, Parabacteroides, Clostridium* IV, *Ruminococcus, Blautia, Dorea, Ruminococcus*2, and *Clostridium* XVIII in the subject's gut.

In an aspect, the present disclosure provides a treatment regimen that is capable of achieving a primary outcome rate of at least two fold higher relative to a primary outcome rate from placebo, where the primary outcome is defined as a steroid-free clinical remission and endoscopic remission or response at the end of the treatment regimen, where the clinical remission is defined as a total Mayo score of 2 or lower with all sub-scores of 1 or lower, and where the endoscopic remission or response is defined as a reduction of at least 1 point from baseline in Mayo endoscopy score. In one aspect, the present disclosure provides a treatment regimen that is capable of achieving a primary outcome rate higher than a primary outcome rate from placebo, where the primary outcome is defined as a steroid-free clinical remission and endoscopic remission or response at the end of the treatment regimen, where the clinical remission is defined as a total Mayo score of 2 or lower with all sub-scores of 1 or lower, and where the endoscopic remission or response is defined as a reduction of at least 1 point from baseline in Mayo endoscopy score.

In one aspect, a treatment regimen in accordance with the present disclosure is capable of achieving a primary outcome rate of at least 25%, such as at least 20%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a treatment regimen is capable of achieving a primary outcome rate of between 20% to 40%, such as between 20% and 35%, between 25% and 40%, between 25% and 35%, between 25% and 30%, or between 30% and 35%.

In one aspect, a treatment regimen in accordance with the present disclosure is capable of achieving a clinical remission sustaining rate of at least 40% at 8 weeks after the completion of the treatment regimen. In an aspect, a treatment regimen is capable of achieving a clinical remission sustaining rate of at least 45%, such as at least 50%, at least 55%, at least 60%, at least 65%, at least 70%, at least 75%, at least 80%, at least 85%, at least 90%, at least 95%, at least 98%, at least 99%, at least 99.5%, or at least 99.9% at 8 weeks after the completion of the treatment regimen. In an aspect, a treatment regimen is capable of achieving a clinical remission sustaining rate of between 35% and 60%, such as between 35% and 55%, between 40% and 60%, between 40% and 55%, between 40% and 50%, between 45% and 55%, or between 45% and 50% at 8 weeks after the completion of the treatment regimen.

In one aspect, a treatment regimen in accordance with the present disclosure is capable of achieving a steroid-free clinical remission rate of at least two fold higher relative to a steroid-free clinical remission rate from placebo, where the clinical remission is defined as a combined Mayo score of 1 or lower for rectal bleeding and stool frequency. In an aspect, a treatment regimen in accordance with the present disclosure is capable of achieving a steroid-free clinical remission rate higher than a steroid-free clinical remission rate from placebo, where the clinical remission is defined as a combined Mayo score of 1 or lower for rectal bleeding and stool frequency. In an aspect, a treatment regimen is capable of achieving a steroid-free clinical remission rate of at least 40%, such as at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In one aspect, a treatment regimen is capable of achieving a steroid-free clinical remission rate of between 35% and 55%, such as between 40% and 55%, between 35% and 50%, between 40% and 50%, between 40% and 45%, or between 45% and 50%.

In an aspect, a treatment regimen in accordance with the present disclosure is capable of achieving a steroid-free clinical response rate of at least two fold higher relative to a steroid-free clinical response rate from placebo, where the clinical response is defined as a total Mayo score decrease of 3 or higher or a 50% higher reduction from baseline in combined score for rectal bleeding and stool frequency. In one aspect, a treatment regimen in accordance with the present disclosure is capable of achieving a steroid-free clinical response rate higher than a steroid-free clinical response rate from placebo, where the clinical response is defined as a total Mayo score decrease of 3 or higher or a 50% higher reduction from baseline in combined score for rectal bleeding and stool frequency. In one aspect, a treatment regimen is capable of achieving a steroid-free clinical response rate of at least 50%, such as at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a treatment regimen in accordance with the present disclosure is capable of achieving a steroid-free clinical response rate between 45% and 65%, such as between 45% and 60%, between 50% and 65%, between 50% and 60%, between 50% and 55%, or between 55% and 60%.

In one aspect, a treatment regimen in accordance with the present disclosure is capable of achieving an endoscopic response rate of at least two fold higher relative to an endoscopic response rate from placebo, where the endoscopic response is defined as a total UCEIS score decrease of 3 or higher or a 50% or higher reduction from baseline. In one aspect, a treatment regimen in accordance with the present disclosure is capable of achieving an endoscopic response rate higher than an endoscopic response rate from placebo, where the endoscopic response is defined as a total UCEIS score decrease of 3 or higher or a 50% or higher reduction from baseline. In an aspect, a treatment regimen is capable of achieving an endoscopic rate of at least 30%, such as at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In one aspect, a treatment regimen is capable of achieving an endoscopic response rate between 30% and 45%, such as between 30% and 40%, between 35% and 45%, or between 35% and 40%.

In one aspect, the present disclosure provides a method for treating ulcerative colitis in a subject in need thereof, where the method comprises administering to the subject a pharmaceutically active dose of a therapeutic composition comprising live non-pathogenic fecal bacteria. In another aspect, this disclosure provides use of a composition comprising live non-pathogenic fecal bacteria in the manufacture of a medication for the treatment of ulcerative colitis.

In some aspects, methods of the present disclosure treat a form of ulcerative colitis selected from the group consisting of ulcerative proctitis, proctosigmoiditis, left-sided colitis, and pan-ulcerative colitis. In an aspect, a pharmaceutical composition in accordance with the present disclosure comprises a fecal microbiota preparation. In one aspect, a pharmaceutical composition comprises an isolated or purified population of live non-pathogenic fecal bacteria. In an aspect, a pharmaceutical composition comprises a non-selective fecal microbiota. In one aspect, a pharmaceutical composition comprises a non-selected and substantially complete fecal microbiota. In an aspect, a pharmaceutical composition comprises a full-spectrum fecal microbiota. In one aspect, a method further comprises administering a 5-aminosalicylic acid agent, a corticosteroid, an immunosuppressant, or a combination thereof. In another aspect, a method further comprises administering 5-aminosalicylic acid or a derivative thereof, sulfasalazine or a derivative thereof, or a combination thereof.

In one aspect, the present disclosure provides a method for selecting a treatment plan for treating ulcerative colitis in a subject in need thereof, where the method comprises determining the level of *Fusobacterium, Sutterella*, or both in the subject's gut; and recommending a fecal bacteria-based therapy when the level of *Fusobacterium, Sutterella*, or both is above a predetermined level. In an aspect, the level of *Fusobacterium, Sutterella*, or both is about 8% above a predetermined level, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, or about 200% above a predetermined level. In an aspect, the present disclosure provides a method for selecting a treatment plan for treating ulcerative colitis in a subject in need thereof, where the method comprises determining the level of *Fusobacterium, Sutterella*, or both in said subject's gut; and recommending a fecal bacteria-based therapy when said level of *Fusobacterium, Sutterella*, or both is between a predetermined range. In one aspect, the predetermined range is about 8% to about 50% above a predetermined level, such as about 8% to about 40%, about 10% to 50%, about 15% to about 40%, about 20% to about 35%, or about 25% to about 30% above a predetermined level. In an aspect, the predetermined range is about 50% to about 200% above a predetermined level, such as about 50% to about 150%, about 50% to about 100%, about 100% to 150%, about 80% to about 120%, about 90% to about 110%, or about 98% to about 100% above a predetermined level. In some aspects, the level of one or more bacteria is determined via analyzing a subject's feces.

In an aspect, the present disclosure provides a method for selecting a treatment plan for treating ulcerative colitis in a subject in need thereof, where the method comprises determining the level of one or more bacteria selected from the group consisting of *Barnesiella, Parabacteroides, Clostridium* IV, *Ruminococcus, Blautia, Dorea, Ruminococcus*2, and *Clostridium* XVIII in said subject's gut; and recommending a fecal bacteria-based therapy when the level of the one or more selected bacteria is above a predetermined level. In an aspect, the level of the one or more selected bacteria is about 8% above a predetermined level, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, or about 200% above a predetermined level. In an aspect, the present disclosure provides a method for selecting a treatment plan for treating ulcerative colitis in a subject in need thereof, where the method comprises determining the level of one or more bacteria selected from the group consisting of *Barnesiella, Parabacteroides, Clostridium* IV, *Ruminococcus, Blautia, Dorea, Ruminococcus*2, and *Clostridium* XVIII in said subject's gut; and recommending a fecal bacteria-based therapy when the level of the one or more selected bacteria is between a predetermined range. In one aspect, the predetermined range is about 8% to about 50% above a predetermined level, such as about 8% to about 40%, about 10% to 50%, about 15% to about 40%, about 20% to about 35%, or about 25% to about 30% above a predetermined level. In an aspect, the predetermined range is about 50% to about 200% above a predetermined level, such as about 50% to about 150%, about 50% to about 100%, about 100% to 150%, about 80% to about 120%, about 90% to about 110%, or about 98% to about 100% above a predetermined level. In some aspects, the level of one or more bacteria is determined via analyzing a subject's feces.

In one aspect, a predetermined level is established by the corresponding level of the one or more selected bacteria in healthy subjects. In an aspect, a predetermined level is established by the corresponding level of the one or more selected bacteria in healthy subjects in the same demographic category as the subject. In one aspect, a predetermined level is established by the abundance of the total *Clostridium* or *Bacteriodetes* population in the same subject.

In one aspect, the present disclosure provides a method which eliminates or reduces one or more ulcerative colitis symptoms selected from the group consisting of diarrhea, cramp, tenesmus, weight loss, bleeding, loss of appetite, abdominal pain, fever, fatigue, anaemia, inflammation, and micro-ulcers.

In one aspect, the present disclosure provides a method for treating ulcerative colitis in a subject in need thereof, where the method comprises administering to the subject a pharmaceutically active dose of a therapeutic composition comprising live non-pathogenic bacteria. In one aspect, the present disclosure provides a method for treating ulcerative colitis in a subject in need thereof, where the method comprises administering daily to the subject a pharmaceutically active dose of a therapeutic composition comprising live non-pathogenic fecal bacteria. In one aspect, a therapeutic composition is administered to an ulcerative colitis patient in need thereof at least once daily for at least two consecutive days. In one aspect, a therapeutic composition is administered at least once daily for at least 3, 4, 5, 6, 7, 8, 9, 10, 11, 12, 13, 14, or 15 consecutive days. In another aspect, a therapeutic composition is administered at least once daily for at least 1, 2, 3, 4, 5, 6, 7, 8, 9, 10, 11, or 12 consecutive weeks. In one aspect, a therapeutic composition is administered at least once daily for at most 4, 5, 6, 7, 8, 9, 10, 11, 12, 13, 14, 15, 16, 17, 18, 19, or 20 consecutive days or weeks. In another aspect, a therapeutic composition is administered at least once daily for at most 1, 2, 3, 4, 5, 6, 7, 8, 9, 10, 11, or 12 consecutive weeks or months. In a further aspect, a therapeutic composition is administered at least once for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an ulcerative colitis patient in need thereof at least twice daily for at least two consecutive days. In one aspect, a therapeutic composition is administered at least twice daily for at least 3, 4, 5, 6, 7, 8, 9, 10, 11, 12, 13, 14, or 15 consecutive days. In another aspect, a therapeutic composition is administered at least twice daily for at least 1, 2, 3, 4, 5, 6, 7, 8, 9, 10, 11, or 12 consecutive weeks. In one aspect, a therapeutic composition is administered at least twice daily for at most 4, 5, 6, 7, 8, 9, 10, 11, 12, 13, 14, 15, 16, 17, 18, 19, or 20 consecutive days or week. In another aspect, a therapeutic composition is administered at least twice daily for at most 1, 2, 3, 4, 5, 6, 7, 8, 9, 10, 11, or 12 consecutive weeks or months. In a further aspect, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an ulcerative colitis patient in need thereof at least three times daily for at least two consecutive days. In one aspect, a therapeutic composition is administered at least three times daily for at least 3, 4, 5, 6, 7, 8, 9, 10, 11, 12, 13, 14, or 15 consecutive days. In another aspect, a therapeutic composition is administered at least three times daily for at least 1, 2, 3, 4, 5, 6, 7, 8, 9, 10, 11, or 12 consecutive weeks. In one aspect, a therapeutic composition is administered at least three times daily for at most 4, 5, 6, 7, 8, 9, 10, 11, 12, 13, 14, 15, 16, 17, 18, 19, or 20 consecutive days or weeks. In another aspect, a therapeutic composition is administered at least three times daily for at most 1, 2, 3, 4, 5, 6, 7, 8, 9, 10, 11, or 12 consecutive weeks or months. In a further aspect, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one aspect, the present disclosure provides a method for treating ulcerative colitis in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily for at least three consecutive days or weeks. In another aspect, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one aspect, the present disclosure provides a method for treating ulcerative colitis in a subject in need thereof, where the method comprises a first dosing schedule followed by a second dosing schedule. In one aspect, a first dosing schedule comprises a treatment or induction dose. In one aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In one aspect, a second dosing schedule lasts permanently, for a treated subject's entire life span, or an indefinite period of time. In one aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In one aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In one aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In one aspect, a subject being treated is a subject already with ulcerative colitis. Administration of a disclosed therapeutic composition to clinically, asymptomatic human subject who is genetically predisposed or prone to ulcerative colitis is also useful in preventing the onset of clinical symptoms of ulcerative colitis. A human subject genetically predisposed or prone to ulcerative colitis can be a human subject having a close family member or relative exhibiting or having suffered ulcerative colitis. In another aspect, a subject being treated is a subject in which ulcerative colitis is to be prevented. In another aspect, a subject being treated is predisposed or susceptible to ulcerative colitis. In another aspect, a subject being treated is a subject diagnosed as having ulcerative colitis. In one aspect, a subject being treated is a patient in need thereof.

In one aspect, a subject being treated is a human patient. In one aspect, a patient is a male patient. In one aspect, a patient is a female patient. In one aspect, a patient is a premature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

In one aspect, a method comprises administering a therapeutic composition orally, by enema, or via rectal suppository. In one aspect, a therapeutic composition administered herein is formulated as an enteric coated (and/or acid-resistant) capsule or microcapsule, or formulated as part of or administered together with a food, a food additive, a dairy-based product, a soy-based product or a derivative thereof, a jelly, or a yogurt. In another aspect, a therapeutic composition administered herein is formulated as an acid-resistant enteric coated capsule. A therapeutic composition can be provided as a powder for sale in combination with a food or drink. A food or drink can be a dairy-based product or a soy-based product. In another aspect, a food or food supplement contains enteric-coated and/or acid-resistant microcapsules containing a therapeutic composition.

In an aspect, a therapeutic composition comprises a liquid culture. In another aspect, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In one aspect, a powder may be reconstituted to be infused via naso-duodenal infusion.

In another aspect, a therapeutic composition administered herein is in a liquid, frozen, freeze-dried, spray-dried, lyophilized, or powder form. In a further aspect, a therapeutic composition administered herein is formulated as a delayed or gradual enteric release form. In another aspect, a therapeutic composition administered herein comprises an excipient, a saline, a buffer, a buffering agent, or a fluid-glucose-cellobiose agar (RGCA) media. In another aspect, a therapeutic composition administered herein comprises a cryoprotectant. In one aspect, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In one aspect, a therapeutic composition administered herein further comprises an acid suppressant, an antacid, an H2 antagonist, a proton pump inhibitor or a combination thereof. In one aspect, a therapeutic composition administered herein substantially free of non-living matter. In another aspect, a therapeutic composition administered herein substantially free of acellular material selected from the group consisting of residual fiber, DNA, viral coat material, and non-viable material.

In one aspect, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one aspect, a method further comprises pretreating a subject with an antibiotic composition prior to administering a therapeutic bacterial or microbiota composition. In one aspect, an antibiotic composition administered herein comprises an antibiotic selected from the group consisting of rifabutin, clarithromycin, clofazimine, vancomycin, rifampicin, nitroimidazole, chloramphenicol, and a combination thereof. In another aspect, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a therapeutic bacterial or microbiota composition.

In one aspect, a method achieves a remission, cure, response, or resolution rate of ulcerative colitis of at least about 10%, 15%, 20%, 25%, 30%, 35%, 40%, 45%, 50%, 55%, 60%, 65%, 70%, 75%, 80%, 85%, 90%, 95%, 97%, or 99%. In one aspect, a treatment method achieves a reduction of ulcerative colitis disease activity index (UCDAI) after 8 weeks of treatment by more than 2, 3, 4, 5, 6, 7, 8, 9, 10, or 11. In another aspect, a treatment method achieves a reduction of ulcerative colitis disease activity index (UCDAI) after 8 weeks of treatment by more than 2, 3, 4, 5, 6, 7, 8, 9, 10, or 11 in at least 10%, 20%, 30%, 50%, 60%, 70%, 80%, or 90% patients in a patient population. In one aspect, a treatment method achieves at least 10%, 20%, 30%, 50%, 60%, 70%, 80%, or 90% reduction of ulcerative colitis disease activity index (UCDAI) after 8 weeks of treatment compared to baseline (e.g., immediately prior to treatment). In one aspect, a treatment method achieves at least 10%, 20%, 30%, 50%, 60%, 70%, 80%, or 90% reduction of ulcerative colitis disease activity index (UCDAI) in at least 10%, 20%, 30%, 50%, 60%, 70%, 80%, or 90% patients after 8 weeks of treatment compared to baseline (e.g., immediately prior to treatment).

In a further aspect, a patient is assessed using the Disease Activity Index (DAI) or Mayo score system as described in Schroeder et al., Coated oral 5-aminosalicylic acid therapy for mildly to moderately active ulcerative colitis. *N Eng J Med.* 1987; 317:1625-1629. In one aspect, a treatment method achieves at least 10%, 20%, 30%, 50%, 60%, 70%, 80%, or 90% reduction of Mayo score after 8 weeks of treatment compared to baseline (e.g., immediately prior to treatment). In one aspect, a treatment method achieves at least 10%, 20%, 30%, 50%, 60%, 70%, 80%, or 90% reduction of Mayo score in at least 10%, 20%, 30%, 50%, 60%, 70%, 80%, or 90% patients after 8 weeks of treatment compared to baseline (e.g., immediately prior to treatment).

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cfu. In another aspect, a pharmaceutically active therapeutic effective dose comprises at most about $10^5$, $10^6$, $10^7$, $10^8$, $10^9$, $10^{10}$, $10^{11}$, $10^{12}$, or $10^{13}$ cfu. In a further aspect, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cells or spores. In another aspect, a pharmaceutically active or therapeutic effective dose comprises at most about $10^5$, $10^6$, $10^7$, $10^8$, $10^9$, $10^{10}$, $10^{11}$, $10^{12}$, or $10^{13}$ total cells or spores. In a further aspect, a pharmacologically active or therapeutic effective dose is selected from the group consisting of from $10^8$ to $10^{14}$, from $10^9$ to $10^{13}$ from $10^{10}$ to $10^{12}$ from $10^9$ to $10^{14}$ from $10^9$ to $10^{12}$ from $10^9$ to $10^{11}$ from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutic effective dose cell count is directed to live cells.

In one aspect, a therapeutic composition administered herein comprises fecal bacteria. In one aspect, a therapeutic composition administered herein comprises one or more, two or more, three or more, four or more, or five or more isolated, purified, or cultured microorganisms selected from the group consisting of Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea, and Monilia.

In one aspect, a therapeutic composition administered herein comprises at least one, at least two, at least three, at least four, at least five, at least six, or at least seven fecal microorganisms selected from the group consisting of a Bacteroides fragilis ssp. vulgatus, Collinsella aerofaciens, Bacteroides fragilis ssp. thetaiotaomicron, Peptostreptococcus productus II, Parabacteroides distasonis, Fusobacterium prausnitzii, Coprococcus eutactus, Collinsella aerofaciens III, Peptostreptococcus productus I, Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis ssp. A, Eubacterium biforme, Bifidobacterium infantis, Eubacterium rectale Coprococcus comes, Pseudoflavonifractor capillosus, Ruminococcus albus, Dorea fonnicigenerans, Eubacterium hallii, Eubacterium ventriosum I, Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis ssp. fragilis, Bacteroides AR, Coprococcus catus, Aerostipes hadrus, Eubacterium cylindroides, Eubacterium ruminantium, Eubacterium CH-1, Staphylococcus epidermidis, Peptostreptococcus BL, Eubacterium limosum, Tissirella praeacuta, Bacteroides L, Fusobacterium mortiferum I, Fusobacterium naviforme, Clostridium innocuum, Clostridium ramosum, Propionibacterium acnes, Ruminococcus flavefaciens, Ruminococcus AT, Peptococcus AU-1, Bacteroides fragilis ssp. ovatus, -ssp. d, -ssp. f; Bacteroides L-1, L-5; Fusobacterium nucleatum, Fusobacterium mortiferum, Escherichia coli, Gemella morbillorum, Finegoldia magnus, Peptococcus G, -AU-2; Streptococcus intermedius, Ruminococcus lactaris, Ruminococcus CO Gemmiger X, Coprococcus BH, -CC; Eubacterium tenue, Eubacterium ramulus, Bacteroides clostridiiformis ssp. clostridliformis, Bacteroides coagulans, Prevotella oralis, Prevotella ruminicola, Odoribacter splanchnicus, Desuifomonas pigra, Lactobacillus G, Succinivibrio A, and a combination thereof.

In one aspect, a therapeutic composition administered herein comprises no viable Bacteroides, Fusobacterium, Propionibacterium, Lactobacillus, Ruminococcus, Escherichia coli, Gemmiger, Desulfomonas, Peptostreptococcus, Bifidobacterium, Monilia, or any combination thereof. In another aspect, a therapeutic composition administered herein comprises no viable Bacteroides fragilis ssp. vulgatus, Collinsella aerofaciens, Bacteroides fragilis ssp. thetaiotaomicron, Peptostreptococcus productus II, Parabacteroides distasonis, Fusobacterium prausnitzii, Coprococcus eutactus, Collinsella aerofaciens III, Peptostreptococcus productus I, Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis ssp. A, Eubacterium biforme, Bifidobacterium infantis, Eubacterium rectale III-F, Coprococcus comes, Pseudoflavonifractor capillosus, Ruminococcus albus, Dorea formicigenerans, Eubacterium hallii, Eubacterium ventriosum I, Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis ssp. fragilis, Bacteroides AR, Coprococcus catus, Aerostipes hadrus, Eubacterium cylindroides, Eubacterium ruminantium, Eubacterium CH-1, Staphylococcus epidermidis, Peptostreptococcus BL, Eubacterium limosum, Tissirella praeacuta, Bacteroides L, Fusobacterium mortiferum I, Fusobacterium naviforme, Clostridium innocuum, Clostridium ramosum, Propionibacterium acnes, Ruminococcus flavefaciens, Ruminococcus AT, Peptococcus AU-1, Bacteroides fragilis ssp. ovatus, -ssp. d, -ssp. f; Bacteroides L-1, L-5; Fusobacterium nucleatum, Fusobacterium mortiferum, Escherichia coli, Gemella morbillorum, Finegoldia magnus, Peptococcus G, -AU-2; Streptococcus intermedius, Ruminococcus lactaris, Ruminococcus CO Gemmiger X, Coprococcus BH, -CC; Eubacterium tenue, Eubacterium ramulus, Bacteroides clostridiiformis ssp. clostridliformis, Bacteroides coagulans, Prevotella oralis, Prevotella ruminicola, Odoribacter splanchnicus, Desuifomonas pigra, Lactobacillus G, Succinivibrio A, or a combination thereof.

In one aspect, a therapeutic composition administered herein comprises a fecal microbiota. In another aspect, the preparation of a fecal microbiota used herein involves a treatment selected from the group consisting of ethanol treatment, detergent treatment, heat treatment, irradiation, and sonication. In another aspect, the preparation of a fecal microbiota used herein involves no treatment selected from the group consisting of ethanol treatment, detergent treatment, heat treatment, irradiation, and sonication. In one aspect, the preparation of a fecal microbiota used herein involves a separation step selected from the group consisting of density gradients, filtration (e.g., sieves, nylon mesh), and chromatography. In another aspect, the preparation of a fecal microbiota used herein involves no separation step selected from the group consisting of density gradients, filtration (e.g., sieves, nylon mesh), and chromatography. In another aspect, a fecal microbiota used herein comprises a donor's entire fecal microbiota. In another aspect, a therapeutic composition administered herein comprises a fecal microbiota substantially free of eukaryotic cells from the fecal microbiota's donor.

In another aspect, a therapeutic composition administered herein comprises a fecal microbiota further supplemented, spiked, or enhanced with a fecal microorganism. In one aspect, a fecal microbiota is supplemented with a non-pathogenic (or with attenuated pathogenicity) bacterium of Clostridium, Collinsella, Dorea, Ruminococcus, Coprococcus, Prevotella, Veillonella, Bacteroides, Baccillus, or a combination thereof. In another aspect, a therapeutic composition administered herein comprises a fecal microbiota further supplemented, spiked, or enhanced with a species of Veillonellaceae, Firmicutes, Gammaproteobacteria, Bacteroidetes, or a combination thereof. In another aspect, a therapeutic composition administered herein comprises a fecal microbiota further supplemented with fecal bacterial spores. In one aspect, fecal bacterial spores are Clostridium spores, Bacillus spores, or both.

In an aspect, a therapeutic composition comprises a fecal microbiota from a subject selected from the group consisting of a human, a bovine, a dairy calf, a ruminant, an ovine, a caprine, or a cervine. In another aspect, a therapeutic composition can be administered to a subject selected from the group consisting of a human, a bovine, a dairy calf, a ruminant, an ovine, a caprine, or a cervine. In an aspect, a therapeutic composition is substantially or nearly odourless.

In an aspect, a therapeutic composition provided or administered herein comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a therapeutic composition comprises a preparation of flora in proportional content that resembles a normal healthy human fecal flora.

In a further aspect, a therapeutic composition comprises fecal bacteria from at least 1, 2, 3, 4, 5, 6, 7, 8, 9, or 10 different families. In a further aspect, a therapeutic composition comprises fecal bacteria from multiple donors. In an aspect, a therapeutic composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a therapeutic composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a therapeutic composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In an aspect, a therapeutic composition provided or administered herein comprises an extract of human feces where the composition is substantially odorless. In an aspect, a therapeutic composition provided or administered herein comprises fecal material or a fecal floral preparation in a lyophilized, crude, semi-purified or purified formulation.

In an aspect, a fecal microbiota in a therapeutic composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, a fecal microbiota in a therapeutic composition comprises a donor's substantially entire or non-selective fecal microbiota, reconstituted fecal material, or synthetic fecal material. In another aspect, the fecal microbiota in a therapeutic composition comprises no antibiotic resistant population. In another aspect, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a therapeutic composition used herein is derived from disease-screened fresh homologous feces or equivalent freeze-dried and reconstituted feces. In an aspect, a fresh homologous feces does not include an antibiotic resistant population. In another aspect, a fecal microbiota in a therapeutic composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea,* and *Ruminococcus*.

In an aspect, a therapeutic composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a therapeutic composition.

In an aspect, a therapeutic composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of ulcerative colitis. The change of flora is preferably as "near-complete" as possible and the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another aspect, a therapeutic composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a therapeutic composition may contain auxiliary substances such as wetting or emulsifying agents, stabilizing or pH buffering agents. In an aspect, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a therapeutic composition contains about 2%-70%, 5%-60%, 10%-50%, 15%-40%, 20%-30%, 25%-60%, 30%-60%, or 35%-60% of active ingredient.

In an aspect, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu). A therapeutic composition used herein can be flavored.

In an aspect, a therapeutic composition can be a tablet or a pill. In one aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a therapeutic composition can be a drench. In one aspect, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a therapeutic composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subtenninale, Clostridium symbiosum, Clostridium tertium, Clostridium tetani, Clostridium welchii*, and *Clostridium villosum.*

In an aspect, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium*, and *Ruminococcus*. In another aspect, a therapeutic composition comprises a plurality of purified, isolated, or cultured viable non-pathogenic microorganisms from one or more genera selected from the group consisting of *Clostridium, Collinsella, Coprococcus, Dorea, Eubacterium*, and *Ruminococcus*.

In an aspect, a therapeutic composition comprises two or more genera selected from the group consisting of *Collinsella, Coprococcus, Dorea, Eubacterium*, and *Ruminococcus*. In another aspect, a therapeutic composition comprises two or more genera selected from the group consisting of *Coprococcus, Dorea, Eubacterium*, and *Ruminococcus*. In a further aspect, a therapeutic composition comprises one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale*, and *Ruminococcus torques.*

In one aspect, a therapeutic composition comprises at least about $10^5$, $10^6$, $10^7$, $10^8$, $10^9$, $10^{10}$, $10^{11}$, $10^{12}$, or $10^{13}$ cfu. In another aspect, a therapeutic composition comprises at most about $10^5$, $10^6$, $10^7$, $10^8$, $10^9$, $10^{10}$, $10^{11}$, $10^{12}$, $10^{13}$ or $10^{14}$ cfu.

In another aspect, a therapeutic composition comprises at least about $10^5$, $10^6$, $10^7$, $10^8$, $10^9$, $10^{10}$, $10^{11}$, $10^{12}$, or $10^{13}$ cells. In another aspect, a therapeutic composition comprises at most about $10^5$, $10^6$, $10^7$, $10^8$, $10^9$, $10^{10}$, $10^{11}$, $10^{12}$, $10^{13}$ or $10^{14}$ cells.

From the foregoing, it will be appreciated that the present invention can be embodied in various ways, which include but not limited to the following embodiments:

1. A method for treating ulcerative colitis (UC) in a subject in need thereof comprising treating the subject with a treatment regimen comprising the administration of a pharmaceutical composition comprising live non-pathogenic fecal bacteria for at least 8 weeks and at least three times per week.

2. A method for treating a condition in a subject in need thereof comprising treating the subject with a treatment regimen comprising the administration of a pharmaceutical composition comprising live non-pathogenic fecal bacteria for at least 8 weeks and at least three times per week, where the condition is selected from the group consisting of collagenous colitis, lymphocytic colitis, Crohn's colitis, diverticulitis, and pouchitis.

3. The method of embodiment 1 or 2, where the treatment regimen is capable of achieving a primary outcome rate of at least two fold higher relative to a primary outcome rate from placebo, where the primary outcome is defined as a steroid-free clinical remission and endoscopic remission or response at the end of the treatment regimen, where the clinical remission is defined as a total Mayo score of 2 or lower with all sub-scores of 1 or lower, where the endoscopic remission or response is defined as a reduction of at least 1 point from baseline in Mayo endoscopy score.

4. The method of embodiment 3, where the treatment regimen is capable of achieving a primary outcome rate of at least 25%.

5. The method of embodiment 3, where the treatment regimen is capable of achieving a primary outcome rate between 20% and 40%.

6. The method of embodiment 3, where the treatment regimen is capable of achieving a clinical remission sustaining rate of at least 40% at 8 weeks after the completion of the treatment regimen.

7. The method of embodiment 3, where the treatment regimen is capable of achieving a clinical remission sustaining rate of between 35% and 60% at 8 weeks after the completion of the treatment regimen.

8. The method of embodiment 1 or 2, where the treatment regimen is capable of achieving a steroid-free clinical remission rate of at least two fold higher relative to a steroid-free clinical remission rate from placebo, where the clinical remission is defined as a combined Mayo score of 1 or lower for rectal bleeding and stool frequency.

9. The method of embodiment 8, where the treatment regimen is capable of achieving a steroid-free clinical remission rate of at least 40%.

10. The method of embodiment 8, where the treatment regimen is capable of achieving a steroid-free clinical remission rate between 35% and 55%.

11. The method of embodiment 1 or 2, where the treatment regimen is capable of achieving a steroid-free clinical response rate of at least two fold higher relative to a steroid-free clinical response rate from placebo, where the clinical response is defined as a total Mayo score decrease of 3 or higher or a 50% or higher reduction from baseline in combined score for rectal bleeding and stool frequency.

12. The method of embodiment 11, where the treatment regimen is capable of achieving a steroid-free clinical response rate of at least 50%.

13. The method of embodiment 11, where the treatment regimen is capable of achieving a steroid-free clinical response rate between 45% and 65%.

14. The method of embodiment 1 or 2, where the treatment regimen is capable of achieving an endoscopic response rate of at least two fold higher relative to an endoscopic response rate from placebo, where the endoscopic response is defined as a total UCEIS score decrease of 3 or higher or a 50% or higher reduction from baseline.

15. The method of embodiment 14, where the treatment regimen is capable of achieving an endoscopic response rate of at least 30%.

16. The method of embodiment 14, where the treatment regimen is capable of achieving an endoscopic response rate between 30% and 45%.

17. The method of embodiment 1 or 2, where the method further comprises determining the subject's baseline gut bacterial diversity.

18. The method of embodiment 17, where the subject's baseline gut bacterial diversity is assessed by analyzing Shannon's diversity of the subject's fecal sample prior to the treating step.

19. The method of embodiment 18, where the subject's fecal Shannon's diversity is between 0.5 and 2.2 based on bacterial species level.

20. The method of embodiment 1 or 2, where the method further comprises determining the level of *Fusobacterium, Sutterella*, or both in the subject's gut.

21. The method of embodiment 1 or 2, where the method further comprises determining the level of one or more bacteria selected from the group consisting of *Barnesiella, Parabacteroides, Clostridium* IV, *Ruminococcus*, Blautia, *Dorea, Ruminococcus*2, and *Clostridium* XVIII in the subject's gut.

22. The method of embodiment 1 or 2, where the pharmaceutical composition comprises a fecal microbiota preparation.

23. The method of embodiment 1 or 2, where the subject exhibits a Mayo score of at least 4 prior to the treating step.

24. The method of embodiment 1 or 2, where the subject exhibits a Mayo score of 4 to 10 prior to the treating step.

25. A method for treating ulcerative colitis (UC) in a subject in need thereof and exhibiting a Mayo endoscopy score of 3 or lower, the method comprising administering to the subject a pharmaceutical composition comprising live non-pathogenic fecal bacteria.

26. The method of embodiment 25, where the administering is following a treatment regimen lasting for at least 8 weeks.

27. The method of embodiment 25, where the administering is following a treatment regimen of at least 8 weeks and at least three times per week.

28. The method of embodiment 27, where the subject is capable of achieving a primary outcome at the end of the treatment regimen, where the primary outcome is defined as a steroid-free clinical remission and endoscopic remission or response at the end of the treatment regimen, where the steroid-free clinical remission is defined as a total Mayo score of 2 or lower with all sub-scores of 1 or lower, where the endoscopic remission or response is defined as a reduction of at least 1 point from baseline in endoscopy score.

29. The method of embodiment 25, where the administering step is following a treatment regimen of daily for at least 8 weeks.

30. A method for treating ulcerative colitis (UC) in a subject in need thereof, the method comprising administering to the subject a pharmaceutical composition comprising live non-pathogenic fecal bacteria, where the subject has no concomitant corticosteroid use during said method and has no corticosteroid use immediately prior to commencing the method.

31. The method of embodiment 30, where the subject has no steroid use within at least one week prior to commencing the method.

32. The method of embodiment 30, where the subject has no corticosteroid use within at least one week prior to commencing the method.

33. The method of embodiment 30, where the subject has no corticosteroid use prior to commencing the method.

34. The method of embodiment 30, where the administering is following a regimen lasting for at least 8 weeks.

35. The method of embodiment 30, where the administering is following a regimen of at least 8 weeks and at least three times per week.

36. The method of embodiment 35, where the subject is capable of achieving a primary outcome at the end of the regimen, where the primary outcome is defined as a steroid-free clinical remission and endoscopic remission or response at the end of the treatment regimen, where the steroid-free clinical remission is defined as a total Mayo score of 2 or lower with all sub-scores of 1 or lower, where the endoscopic remission or response is defined as a reduction of at least 1 point from baseline in endoscopy score.

37. A method for selecting a treatment plan for treating ulcerative colitis (UC) in a subject in need thereof, the method comprising determining the level of *Fusobacterium, Sutterella*, or both in the subject's gut; and recommending a fecal bacteria-based therapy when the level of *Fusobacterium, Sutterella*, or both is below a predetermined level.

38. A method for selecting a treatment plan for treating ulcerative colitis (UC) in a subject in need thereof, the method comprising determining the level of one or more bacteria selected from the group consisting of *Barnesiella, Parabacteroides, Clostridium* IV, *Ruminococcus*, Blautia, *Dorea, Ruminococcus*2, and *Clostridium* XVIII in the subject's gut; and recommending a fecal bacteria-based therapy when the level of one or more bacteria selected from the group consisting of is above a predetermined level.

39. The method of embodiment 37 or 38, where the level of one or more bacteria is determined via analyzing said subject's feces.

EXAMPLES

Example 1. Patient Selection Criteria

Patients, including males and females aged 18 to 75 years, who have clinically and endoscopically active ulcerative colitis, with a total Mayo score of 4-10, which incorporates stool frequency, rectal bleeding, mucosal appearance at endoscopy, and physician's global assessment (PGA) are included. The endoscopy score has to be ≥1 and PGA score ≤2. Furthermore, such ulcerative colitis has to be present for more than three months in duration. Ulcerative colitis of any extent is treated except for isolated proctitis that are <5 cm. See Table 4 for all inclusion criteria.

TABLE 4

Study Participant Inclusion Criteria
Patients must meet all the following INCLUSION CRITERIA at enrolment to be eligible to participate 1. Males and females aged 18 to 75 years, inclusive
2. Ulcerative colitis >3 months duration
3. Ulcerative Colitis of any extent except isolated proctitis <5 cm
4. Currently active mild-moderate ulcerative colitis, as measured by a Mayo score of 4-10, which incorporates stool frequency, rectal bleeding, mucosal appearance, and physician's assessment as a four point category score. Endoscopy score must be ≥1 and physician global assessment score ≤2
5. Provide written informed consent to participate as shown by a signature on the consent form Patients receiving treatment with oral 5-aminosalicylates, thiopurines and methotrexate has to be at stable doses. Oral prednisolone is allowed in patients. Patients having undergone a mandatory oral prednisolone may taper of up to 2.5 mg per week, and need to be steroid-free by week 8.

Patients receiving rectal therapies in the past 2 weeks, receiving antibiotics or probiotics in the past 4 weeks, and receiving biologic therapy in the past 12 weeks are to be excluded. Patients exhibiting evidence or history of toxic megacolon, as well as any other significant gastrointestinal conditions, including but not limited to irritable bowel syndrome, diverticulitis, and neoplasm, are also excluded. Patients being diagnosed of Crohn's disease or indeterminate colitis are excluded. Patients with perianal disease such as fistulae and pre-existing fissures are excluded. Patients with severe anaemia, leucopaenia, or granulocytopenia are excluded. Patients who had appendectomy less than 3 months prior to treatment are also excluded. Patients with significant food hypersensitivity are excluded. See Table 5 for all exclusion criteria.

TABLE 5

Study Participant Exclusion Criteria
Patients must not meet any of the following EXCLUSION CRITERIA at enrolment to be eligible to participate 1. Consent not obtained or unable to give informed consent
2. Unable to communicate with the investigators and comply with the study requirements
3. Females who are pregnant or actively trying to fall pregnant
4. Patients unwilling to practice an effective method of contraception throughout the study period
5. Patients defined as in remission by the investigator
6. Patients with mild ulcerative colitis (Mayo score <4)
7. Patients with severe ulcerative colitis (Mayo score >10)
8. Evidence or history of toxic megacolon
9. Isolated proctitis <5 cm
10. A diagnosis of Crohn's Disease or indeterminate colitis
11. Patients with perianal disease (e.g. fistulae, pre-existing fissures)
12. Severe anaemia, leucopaenia or granulocytopenia
13. Detection of a gastrointestinal pathogen on stool analysis
Need to exclude/treat active GI infection before inclusion into study (e.g. *giardia*, *C. diff*, CMV etc.)
Prior GI infection is not an exclusion to enrolment as long as successful treatment and eradication is documented
14. Constipation-predominant Ulcerative Colitis with <3 bowel motions/day
15. Any other significant GI condition e.g. Irritable bowel syndrome, diverticulitis, neoplasm etc.
16. Significant gastrointestinal surgery e.g. colon resection, colectomy
Minor gastrointestinal surgery will be reviewed on a case by case basis by the investigator
Regarding appendicectomy, only exclude patients who had appendicectomy <3 months ago
17. Patients taking antimicrobials (antibiotics, antifungals, antivirals) for any reason, including antibiotics for ulcerative colitis, in the preceding four weeks
18. Patients who are steroid dependent and requiring >20 mg prednisone or >9 mg budesonide daily at the time of enrolment
19. Patients who have recently taken or are actively taking or expected to require prohibited medication/s during the study period including follow-up. These include
Treatment with anti-tumour necrosis factor agents e.g. infliximab, adalimumab, within the last 12 weeks
Treatment with other major immunosuppressant agents including calcineurin inhibitors, mammalian target of rapamycin (mTOR) inhibitors, chemotherapeutic anti-neoplastic agents, lymphocyte depleting biological agents within the last 12 weeks
Probiotic therapy in the last 4 weeks
Experimental/trial drug protocol involvement in last 12 weeks
Anti-mycobacterial (TB or MAC) therapy in last 4 weeks
20. Clinical evidence of any major, co-morbid chronic disease that may interfere with the patient's ability to enter the trial. Patients with a concomitant illness sufficiently severe as to jeopardize participation in the study or interpretation of results will be excluded from the study
In particular, severe immunodeficiency including but not limited to decompensated liver cirrhosis, advanced HIV/AIDS and recent bone marrow transplant will be an absolute contraindication to FMT
21. Patients with food hypersensitivity deemed by the investigator to be significant during the trial e.g., nut allergy
22. Patients who have travelled overseas to an infectious diarrhea endemic area within the last month or have overseas travel planned during the study period (not feasible to be compliant with enema therapy)

Based on the above criteria, eighty-five patients are recruited in this study. The selected patients are randomized with 81 commencing treatment (FIG. 1). The two groups are well matched except for disease severity; significantly more patients with the mildest (Mayo 1) endoscopic disease are randomized to placebo. Table 6 summarizes the baseline characteristics of the recruited patients.

TABLE 6

Baseline Patient Characteristics.

|  | FJIT (n = 41.) | Placebo (n = −40) | P Value |
|---|---|---|---|
| Age, y | 35.5 (27.8-48.9) | 35.4 (27.7-45.6) | 0.97 |
| Male Sex, n (%) | 22 (54%) | 25 (63%) | 0.42 |
| Caucasian race, n (%) | 27 (66%) | 27 (68%) | 0.88 |
| Non Smoker, n (%) | 23 (56%) | 21 (53%) | 0.75 |
| UC < 1 year, n (%) | 2 (5%) | 2 (5%) | 0.98 |
| Disease Duration, y | 5.8 (3.4-9.0) | 5.8 (2.7-9.4) | 0.55 |
| Disease Extent, n (%) |  |  |  |
| Proctitis | 4 (10%) | 8 (20%) | 0.19 |
| Left Sided Colitis | 28 (68%) | 20 (50%) | 0.09 |
| Pancolitis | 9 (22%) | 12 (30%) | 0.41 |
| Concomitant Medications, n (%) |  |  |  |
| Nil | 9 (22%) | 6 (15%) | 0.42 |
| Oral 5-ASA | 26 (63%) | 28 (70%) | 0.53 |
| Oral Immunomodulator | 20 (49%) | 15 (38%) | 0.31 |
| Oral Steroids | 9 (22%) | 11 (28%) | 0.56 |
| Prior Anti-TNIF Therapy, n (1%) | 9 (22%) | 6 (15%) | 0.42 |
| Prior Other Biologic Therapy, n (%) | 2 (5%) | 0 (0%) | 0.16 |
| Mayo Score | 8 (6-9) | 8 (6-9) | 0.43 |
| Mayo Endoscopic Subscore, n (%) |  |  |  |
| Mayo 1 | 1 (2%) | 7 (18%) | 0.02* |
| Mayo 2 | 27 (65%) | 15 (38%) | 0.01* |
| Mayo 3 | 13 (32%) | 18 (45%) | 0.22 |
| UCEIS Score | 4 (3.5-5.5) | 4 (3-5) | 0.76 |
| IBDQ Score | 123 (99-157) | 119 (109-149) | 0.78 |
| Faecal Calprotectin, ug/g | 705 (226-1220) | 505 (193-1475) | 0.41 |
| Erythrocyte Sedimentation Rate, mm/hr | 14 (5.5-29.5) | 10 (5-20) | 0.20 |
| C -Reactive Protein, mg/L | 2.6 (1.0-7.1) | 2.9 (0.8-5.8) | 0.93 |
| White Cell Count. $\times 10^9$/L | 7.8 (6.2-9.7) | 8.0 (6.3-9.9) | 0.71 |
| Neutrophil Count, $\times 10^9$/L | 4.8 (3.5-6.9) | 5.7 (3.7-6.7) | 0.60 |
| Haemoglobin, g/L | 134 (129-143) | 136 (127-148) | 0.56 |
| Platelet Count, $\times 10^9$/L | 299 (248-352) | 306 (251-362) | 0.48 |
| Albumin, g/L | 46 (43-48) | 45 (43-48) | 0.50 |

Example 2. Stool Donors Selection

Stool donors, including males and females aged 18 to 65 years, who have no history or current symptoms of gastrointestinal disease including but not limited to inflammatory bowel disease and irritable bowel syndrome are included. Donors should not have any major active medical co-mobidities. Donors should have minimal regular medications with no medications that may interfere with stool viability, including no antimicrobials, probiotics and proton pump inhibitors in the preceding three months prior to donation. See Table 7 for all donor inclusion criteria.

TABLE 7

Healthy Fecal Donor Inclusion Criteria
Donors must meet all the following INCLUSION CRITERIA at enrolment 1. Males and females aged 18 to 65 years, inclusive
2. No history or current symptoms of gastrointestinal disease including but not limited to inflammatory bowel disease (IBD) and irritable bowel syndrome (IBS)

TABLE 7-continued

Healthy Fecal Donor Inclusion Criteria
Donors must meet all the following INCLUSION CRITERIA at enrolment 3. No other major active medical co-morbidities
4. Minimal regular medications with no medications that may interfere with stool viability
including no antimicrobials (antibiotics, antivirals,antifungals), probiotics and proton pump inhibitors (PPIs) in the preceding 3 months
5. Provide written informed consent to participate as shown by a signature on the consent form To exclude unhealthy donors, a potential donor's stool is evaluated using one or more of the following tests: *Clostridium difficile* toxin PCR, fecal microscopy/culture/ sensitivity with routine bacterial culture for enteric pathogens, fecal *Giardia* antigen, fecal *Cyrptosporidium* antigen, fecal ova/cysts/parasites (including *Blastocystis hominis* and *Dientamoeba fragilis*), and Norovirus EIA. A potential donor's blood is also tested for one or more of the following: complete blood count (CBC); electrolytes, urea and creatinine (EUC); liver function tests (LFT); erythrocyte sedimentation rate (ESR); C-Reactive protein (CRP); human immunodeficiency virus (HIV) type 1 and 2; Hepatitis A virus IgM; Hepatitis B virus surface antigen, Hepatitis B virus core antibody (IgM+IgG), Hepatitis B virus surface antibody; Hepatitis C virus antibody; Rapid plasma regain and/or fluorescent treponemal antibody-absorbed; and human T-cell lymphotropic virus (HTLV) 1 and 2.

TABLE 8

Healthy Fecal Donor Exclusion Criteria
Donors must not meet any of the following EXCLUSION CRITERIA at enrolment 1. Risk of infectious agent
Known HIV, hepatitis B or hepatitis C infection
Known exposure to HIV or viral hepatitis within the previous 12 months
High risk sexual behavior (e.g. sexual contact with anyone with HIV/AIDS or viral hepatitis, men
who have sex with men, sex for drugs or money)
Use of illicit drugs
Tattoo or body piercing within the preceding 6 months
Incarceration or history of incarceration
Known current communicable disease (e.g. upper respiratory tract infection)
Risk factors for variant Creutzfeldt-Jakob disease
Travel within last 2 weeks to areas of the world where diarrheal illnesses are endemic or risk of
traveler's diarrhea is high
2. Gastrointestinal co-morbidities
History of or current inflammatory bowel disease (IBD)
History of or current irritable bowel syndrome (IBS), chronic constipation, chronic diarrhea or other
intrinsic gastrointestinal illness/condition
History of or current gastrointestinal malignancy or known polyposis or strong family history of
colorectal cancer
History of major gastrointestinal surgery (e.g. gastric bypass, partial colectomy)
3. Factors that can affect the composition of the intestinal microbiota
Antimicrobials (antibiotics, antivirals, antifungals), probiotics or proton pump inhibitors (PPIs)
within the preceding 3 months
Major immunosuppressive medications (e.g. calcineurin inhibitors, biological agents, exogenous
glucocorticoids)
Systemic anti-neoplastic agents
Household members with active GI infection
4. Other conditions
Systemic autoimmunity (e.g. multiple sclerosis, connective tissue disease)
Atopic disease (e.g. moderate - severe asthma, eosinophilic disorders of the gastrointestinal tract)
Metabolic syndrome, obesity (BMI > 30) or moderate to severe under-nutrition/malnutrition
Chronic pain syndromes (e.g. chronic fatigue syndrome, fibromyalgia) or neurologic/
neurodevelopmental disorders
History of malignant illness or ongoing oncologic therapy Based on the above criteria and tests, 14 donors are selected.

Example 3. FMT and Placebo Preparation and Storage

FMT infusions are constituted from the blended stool of 3 to 7 donors, to increase microbial heterogeneity. Each patient receives all their FMT infusions from the same donor batch to ensure consistency and reproducibility of the infused fecal microbiota.

Placebo infusions comprise isotonic saline. Odorant, brown food colour disodium 4,4'-2,4-dihydroxy-5-hydroxymethyl-1,3-phenylene-bisazodi-1-napthalene sulfonate (to replicate fecal odour and colour respectively), and glycerol cryoprotectant (concentration 10%) are added to the 150 ml placebo and FMT infusions, which are then stored at −80° C.

Three to seven of the selected donors contributes to each of the 21 FMT batches in the study. The use of multiple donors for all infusions is one of the features of this study.

Example 4. Study Design

At three clinical centers patients are randomized 1:1 double-blind to FMT:placebo using permutated blocks of 4, stratified for study site and concomitant corticosteroid use.

After full bowel preparation, colonoscopy is performed to the terminal ileum and the initial infusion administered. Patients then self-administer enemas 5 times per week for 8 weeks. After 8 weeks mucosal inflammation is assessed with sigmoidoscopy.

After the initial 8 week study period placebo-treated patients are offered 8 weeks of open-label FMT enemas 5 times per week, without initial colonoscopic infusion. Sigmoidoscopy is repeated after open-label FMT.

Figure 2:
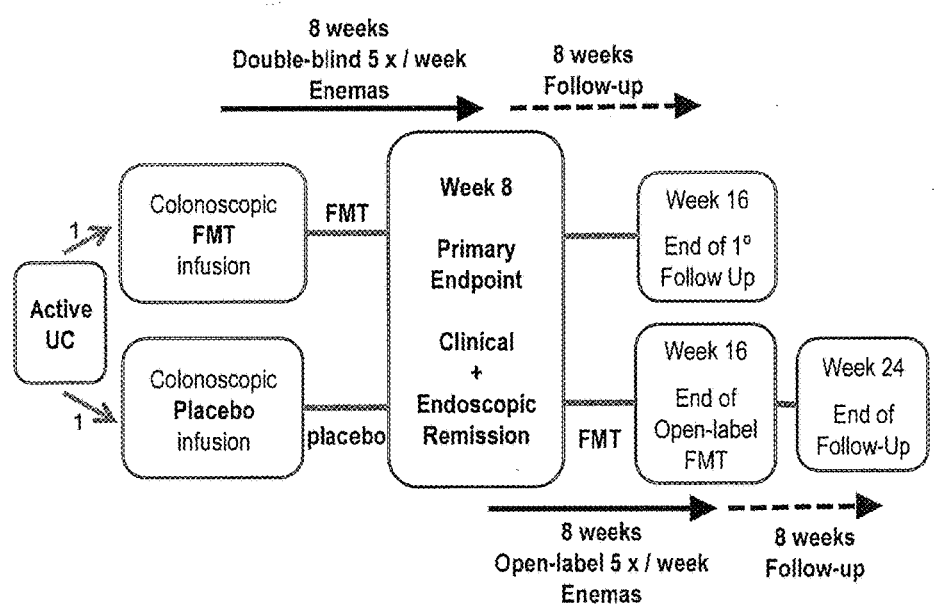
FIG. 2 shows a graphical representation of the study design in accordance with Example 4 of the present disclosure.

FIG. 2 shows a graphical representation of this study design.

Example 5. Study Assessments and Endpoints

Patients are reviewed fortnightly during blinded and open label study periods with a final review 8 weeks post FMT. Blood and stool investigations are performed every 4 weeks during study therapy. Blood tests include CBC, EUC, LFT, ESR, and CRP. Stool tests include fecal calprotectin.

Evaluation of the site of worst inflammation at each endoscopy, using the Mayo endoscopy sub-score and UCEIS score, is undertaken with blinded review and central consensus scoring of all endoscopic photo images by 5 IBD-expert gastroenterologists.

The primary composite outcome is steroid-free clinical remission together with endoscopic remission or response at week 8, defined as a total Mayo score of ≤2 with all sub-scores ≤1 and ≥1 point reduction from baseline in endoscopy score.

Eleven of 41 (27%) FMT-treated patients and 3 of 40 (8%) placebo-treated patients achieve the primary outcome (P=0.02, OR 4.5 (95% CI 1.2-17.7)) (FIG. 3A, FIG. 4A-D).

Figure 3A:
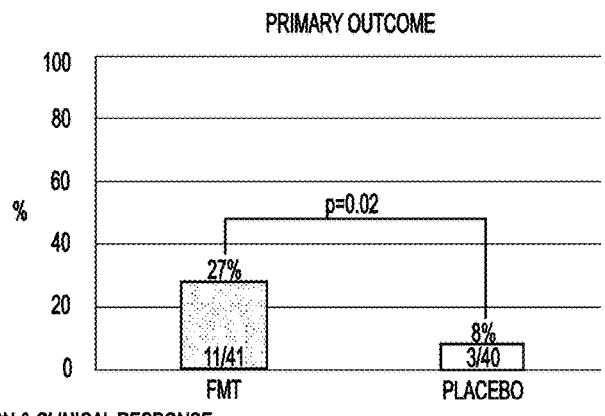
FIG. 3A shows the number of patients in the FMT and placebo-treated groups achieving the primary outcome of steroid-free clinical remission and endoscopic remission or response at week 8 after therapy in accordance with Example 5 of the present disclosure.

FIG. 3A shows the number of patients in the FMT and placebo-treated groups who achieved the primary outcome of steroid-free clinical remission and endoscopic remission or response (total Mayo score ≤2 with all sub-scores ≤1 and ≥1 point reduction from baseline in endoscopy sub-score) at week 8. The total Mayo score can range from 0 to 12, and sub-scores range from 0 to 3, with higher scores indicating more severe disease.

Figure 4A:
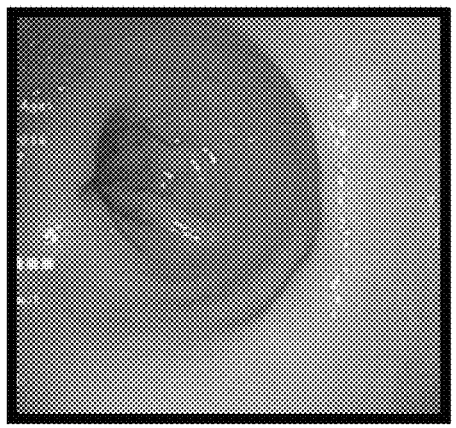
FIG. 4A shows an exemplary baseline endoscopic appearance of 25 cm recto-sigmoid active colitis in accordance with Example 5 of the present disclosure.
Figure 4B:
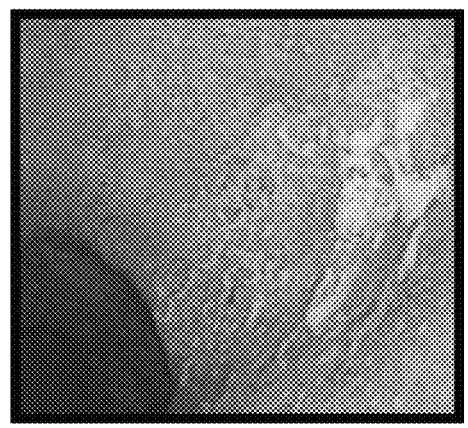
FIG. 4B shows an exemplary endoscopic appearance at end of week 8 blinded FMT therapy in accordance with Example 5 of the present disclosure.

FIG. 4A and FIG. 4B show the effect of a FMT therapy in a 37 year old female patient with a 4 year history of left sided ulcerative colitis and acute colitis (diarrhea 6 times per day with bleeding) despite maximal oral and topical 5-ASA therapy. FIG. 4A shows an exemplary baseline endoscopic appearance of 25 cm recto-sigmoid active colitis with endoscopic Mayo sub-score 2, and total Mayo score 8. FIG. 4B shows an exemplary endoscopic appearance in the same patient at the end of week 8 blinded FMT therapy with endoscopic Mayo sub-score 0, and total Mayo score 0. This patient remains in clinical remission at final study follow up 8 weeks after completing blinded FMT therapy.

Figure 4C:
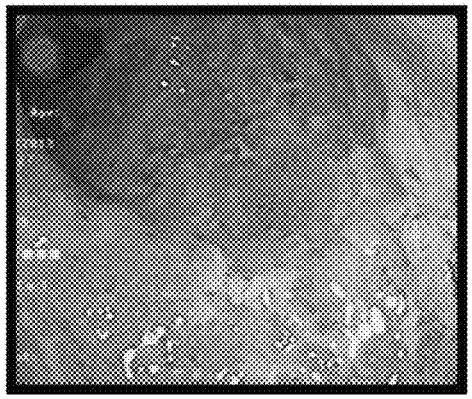
FIG. 4C shows an exemplary baseline endoscopic appearance of extensive colitis to the hepatic flexure in accordance with Example 5 of the present disclosure.
Figure 4D:
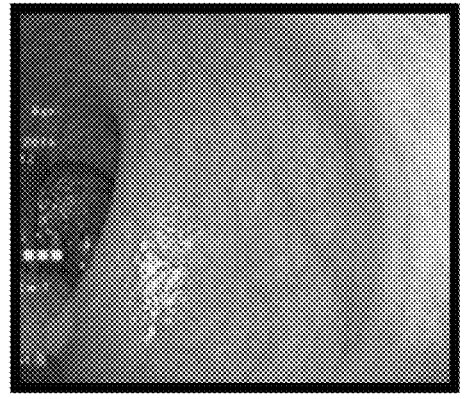
FIG. 4D shows an exemplary endoscopic appearance at the completion of 8 weeks open-label FMT in accordance with Example 5 of the present disclosure.

FIG. 4C and FIG. 4D show the effect of a FMT therapy in a 28 year-old female patient with a 7 year history of extensive ulcerative colitis. This patient experiences failed therapy with mesalamine, probiotic and adalimumab. Accordingly, the patient is maintained on azathioprine and allopurinol, and was steroid-dependent on oral budesonide 9 mg/day. At study entry this patient has diarrhea 8 times per day with bleeding and abdominal pain. FIG. 4C shows an exemplary baseline endoscopic appearance of extensive colitis to the hepatic flexure with endoscopic Mayo sub-score 3, and total Mayo score 10. This patient receives placebo treatment during the primary study, but was unable to taper corticosteroids, and was therefore a treatment failure in the primary outcome. FIG. 4D shows Endoscopic appearance in the same patient at the completion of 8 weeks open-label FMT, with endoscopic Mayo sub-score 0 and Total Mayo Score 0. After 8 weeks of open-label FMT this patient has weaned corticosteroids completely and is in clinical and endoscopic remission.

Secondary outcomes include steroid-free clinical remission (combined score ≤1 for rectal bleeding plus stool frequency Mayo sub-scores), clinical response (decrease ≥3 and/or ≥50% reduction from baseline in combined rectal bleeding plus stool frequency Mayo sub-scores), endoscopic response (Mayo endoscopy sub-score ≤1 with a reduction ≥1 from baseline), complete mucosal healing (Mayo endoscopy sub-score 0), quality of life using IBDQ[10] and safety.

Blinded central reading of all endoscopic images is performed using both Mayo and UCEIS scoring. Assessing steroid free endoscopic outcomes using a decrease ≥3 points and/or ≥50% reduction from baseline in UCEIS score, the difference between the FMT and placebo arms at week 8 was 37% vs. 10%, p<0.01, OR 5.2, 95% CI 1.5-17.5. When the criteria of UCEIS ≤1 is used, the difference between FMT and placebo treated patients was 17% vs. 8%, p=0.19, OR 2.5, 95% CI 0.6-10.6) at week 8.

Significant differences are observed in the total Mayo score, and in the decrease in total Mayo score, at week 8, between the FMT and placebo treated groups (Table 9). IBDQ FMT data is available only from 31 patients. All missing data is assigned worst value in the entire cohort. All continuous variables are reported as median and inter-quartile range.

TABLE 9

Week 8 Efficacy Outcomes.

| Adjusted Outcome Measure | FMT (n = 41, data on 32) | Placebo (n = 40, data on 29) | P Value |
| --- | --- | --- | --- |
| Total Mayo Score at 8 weeks | 4 (2-6) | 7 (4-9) | 0.01 |
| Total Mayo Score decrease at 8 weeks | 4 (2.3-6.0) | 1 (−0.5-2) | <0.01 |
| IBDQ at 8 weeks | 182 (135-206) | 151 (130-195) | 0.21 (NS) |
| IBDCI Improvement at 8 weeks | 40 (15-70) | 23 (10-33) | 0.13 (NS) |
| IBDC/increase of 32 points at 8 weeks | 18 (44%) | 9 (23%) | 0.04 |
| CRP | 2.8 (1.0-1.3) | 3.0 (1.7-4.9) | 0.65 (NS) |
| ESR | 17 (6.5-21) | 11 (6-20) | 0.85 (NS) |
| Calprotectin | 335 (91-1150) | 410 (157-1345) | 0.55 (NS) |

Figure 3B:
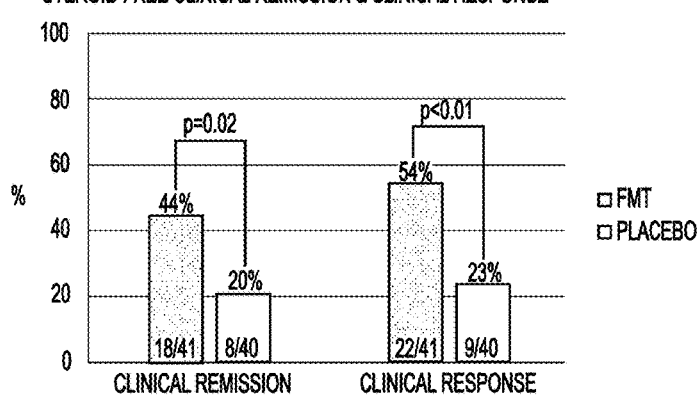
FIG. 3B shows the number of patients in steroid-free clinical remission and clinical response at week 8 after therapy in accordance with the Examples of the present disclosure.

FIG. 3B shows the number of patients in steroid-free clinical remission (combined score of ≤1 for rectal bleeding plus stool frequency Mayo subscores) and clinical response (decrease ≥3 points and/or ≥50% reduction from baseline in the combined score for rectal bleeding plus stool frequency Mayo subscores) at week 8. Steroid-free clinical remission (44% vs. 20%, P=0.02, OR 3.1, 95% CI 1.2-8.4) and steroid-free clinical response (54% vs. 23%, P<0.01, OR 4.0, 95% CI 1.5-10.4) at week 8 is significantly greater in FMT than placebo-treated patients.

Figure 3C:
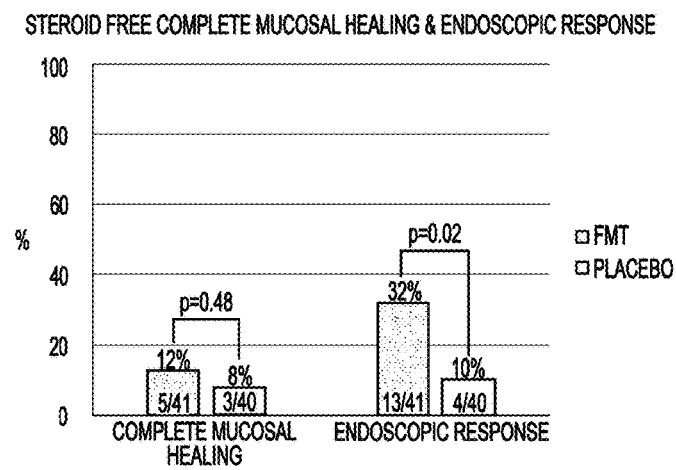
FIG. 3C shows the number of patients with steroid-free endoscopic response and complete mucosal healing after therapy in accordance with the Examples of the present disclosure.
Figure 5:
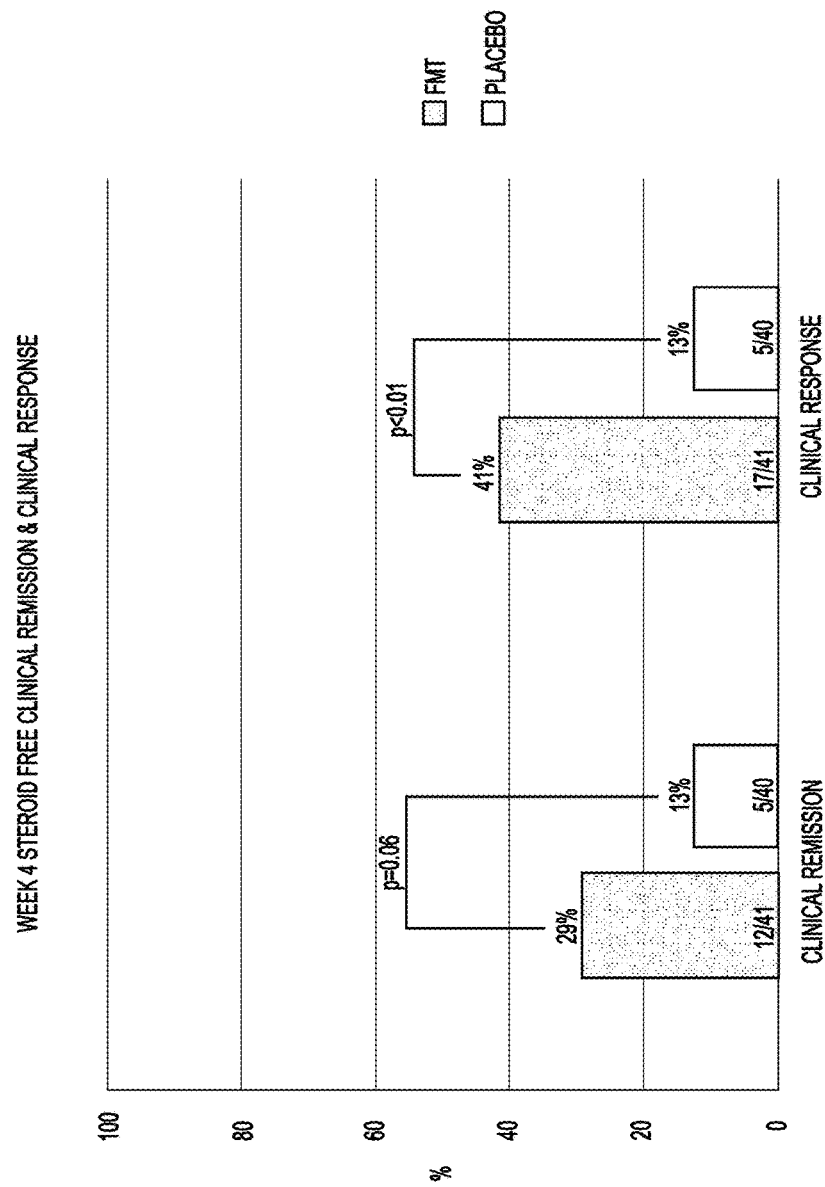
FIG. 5 shows the speed of onset of therapy in accordance with Example 5 of the present disclosure.

FIG. 3C shows the number of patients with steroid-free endoscopic response (Mayo endoscopy sub-score ≤1 with a reduction ≥1 from baseline) and complete mucosal healing (Mayo endoscopy sub-score 0). At week 8 steroid-free endoscopic response (32% vs 10%, P=0.02, OR 4.2, 95% CI 1.2-14.2) is significantly greater in the FMT-treated patients. Complete mucosal healing (Mayo 0: 12% vs. 8%, P=0.48, OR 1.7 95% CI 0.4-7.7) is greater in the FMT than placebo arms but this difference was not significant. Outcomes are similar with UCEIS scoring (FIG. 5). FIG. 5 shows the speed of onset of therapy. At the end of week 4 clinical response is significantly greater in FMT [17 of 41 (41%)] than placebo [5 of 40 (13%)] treated patients (p<0.01, OR 5.0, 95% CI 1.6-15.3]. Clinical remission do not differ significantly between treatment arms [12 of 41 (29%) vs 5 of 40 (13%) respectively (P=0.06, OR 2.9, 95% CI 0.91-9.2)].

IBDQ score and inflammatory markers do not differ significantly between groups (Table 9).

Thirty seven initially placebo-treated patients proceed to open-label FMT. After open-label FMT, 10 (27%) meet the primary endpoint, 17 (46%) are in clinical remission and 8 (22%) have complete mucosal healing.

No relationship between outcome and anatomical disease extent is observed (P=0.23). The severity of endoscopic inflammation is associated with therapeutic outcomes (p=0.01) with no patient with Mayo endoscopy score 3 at study entry achieving the primary outcome. Corticosteroid use is also associated with therapeutic outcome (p=0.02) with no patient entering the study on corticosteroids achieving the primary endpoint at the end of blinded therapy; one patient on corticosteroids at open-label FMT entry meets the primary endpoint at completion.

Sixty-three patients attend a final study follow-up 8 weeks after completing double-blind or open-label FMT, of whom 28 are in clinical remission and 20 require UC therapy escalation.

Nine patients on blinded FMT and 11 on placebo (P=0.56) withdraw or have protocol failure prior to week 8. The reasons for withdrawal or protocol failure on blinded therapy include disease worsening on steroid wean (3 FMT, 6 placebo), disease persistence or worsening in the absence of steroid wean (5 FMT, 3 placebo) and non-compliance (1 FMT, 2 placebo).

Eleven patients who commence open label FMT either withdraw or have a protocol failure: 5 have disease worsening on steroid wean, 2 have disease persistence or worsening in the absence of steroid wean, 4 are non-compliant.

Thirty two (78%) FMT and 33 (83%) placebo-treated patients experience at least one adverse event during blinded therapy, with no significant difference in number or type of adverse events (Table 10). The most common adverse events are self-limiting gastrointestinal complaints (abdominal pain, bloating, and flatulence). Six serious adverse events (SAEs) occur during study therapy: 2 blinded FMT, 1 placebo, 3 open label FMT. One patient with refractory colitis on blinded FMT withdraw at week 2 due to clinical and endoscopic (Mayo 2 to 3, UCEIS 5 to 7) deterioration, and underwent colectomy. One patient with moderate to severe colitis remain unwell at week 3 of blinded active therapy, withdraw and is hospitalized for intravenous corticosteroid therapy. One patient with moderate to severe colitis is withdrawn at week 3 of placebo therapy and require hospitalization. Three initial placebo-treated patients fail to improve with open-label FMT and were hospitalized for escalation of therapy.

TABLE 10

Adverse Events.

| Adverse Event | FMT (n = 41) | Placebo (n = 40) | P Value | Open Label (n = 37) | Follow Up (n = 63) |
|---|---|---|---|---|---|
| Total AE | 78 | 80 | 0.78 (NS) | 35 | 14 |
| Total Patients with AE | 32 (78%) | 33 (83%) | 0.62 (NS) | 18 (49%) | 9 (14%) |
| Total infection Related AE | 11 | 17 | 0.22 (NS) | 9 | 3 |
| Total Patients with Infection Related AE | 10 (24%) | 14 (35%) | 0.30 (NS) | 8 (22%) | 3 (5%) |
| Abdominal pain | 12 (29%) | 11 (28%) | 0.86 (NS) | 5 (14%) | 1 (2%) |
| Colitis | 10 (24%) | 9 (23%) | 0.84 (NS) | 3 (8%) | 4 (6%) |
| Flatulence | 10 (24%) | 8 (20%) | 0.64 (NS) | 2 (5%) | |
| Bloating | 8 (20%) | 11 (28%) | 0.40 (NS) | 3 (8%) | |
| Upper Respiratory Tract Infection | 7 (17%) | 6 (15%) | 0.80 (NS) | 4 (11%) | 2 (3%) |
| Headache | 4 (10%) | 2 (5%) | 0.41 (NS) | 2 (5%) | |
| Dizziness | 3 (7%) | 3 (8%) | 0.97 (NS) | — | |
| Fever | 3 (7%) | 2 (5%) | 0.67 (NS) | — | |
| Rash | 3 (7%) | — | | — | |
| Nausea | 2 (5%) | 5 (13%) | 0.22 (NS) | 1 (3%) | |
| ALT elevated | 2 (5%) | 2 (5%) | 0.98 (NS) | — | 1 (2%) |
| Chills | 2 (5%) | 2 (5%) | 0.98 (NS) | — | 1 (2%) |
| Vomiting | 2 (5%) | 1 (3%) | 0.57 (NS) | — | |
| Back pain | 2 (5%) | — | | — | |
| Flu like symptoms | 1 (2%) | 4 (10%) | 0.16 (NS) | 3 (8%) | |
| Enterocoritis | 1 (2%) | 3 (8%) | 0.29 (NS) | — | |
| Diarrhoea | 1 (2%) | — | | 1 (3%) | |
| Fracture (foot) | 1 (2%) | — | | — | |
| Reflux symptoms | 1 (2%) | — | | — | |
| Sinusitis | 1 (2%) | — | | — | |
| Haemorrhoids | 1 (2%) | — | | — | |
| Elective Surgical procedure | 1 (2%) | — | | — | |
| Anxiety | — | 1 (3%) | | 1 (3%) | 1 (2%) |
| Lung infection | — | 1 (3%) | | 1 (3%) | |
| Anal Fissure | — | 1 (3%) | | — | |
| Faecal Incontinence | — | 1 (3%) | | — | |
| Fatigue | — | 1 (3%) | | — | |
| Genital herpes | — | 1 (3%) | | — | |
| Irritability | — | 1 (3%) | | — | |
| Lip Infection | — | 1 (3%) | | — | |
| Otitis media | — | 1 (3%) | | — | |
| Sore throat | — | 1 (3%) | | — | |
| Urticarial | — | 1 (3%) | | — | |
| Arthralgia | — | — | | 1 (3%) | |
| AST elevated | — | — | | 1 (3%) | |
| Blurred vision | — | — | | 1 (3%) | |
| Depression | — | — | | 1 (3%) | |
| Dry skin | — | — | | 1 (3%) | |
| Insomnia | — | — | | 1 (3%) | |
| Myalgia | — | — | | 1 (3%) | |
| Palpitations | — | — | | 1 (3%) | |
| Productive cough | — | — | | 1 (3%) | |
| Anaemia | — | — | | — | 1 (2%) |
| Non Elective Surgical Procedure (intraoperative | — | — | | — | 1 (2%) |
| Soft tissue infection (Axillary abscess) | — | — | | — | 1 (2%) |

TABLE 10-continued

Adverse Events.

| Adverse Event | FMT (n = 41) | Placebo (n = 40) | P Value | Open Label (n = 37) | Follow Up (n = 63) |
|---|---|---|---|---|---|
| Tremor | — | — | — | — | 1 (2%) |
| Total SAE | 2 (5%) | 1 (3%) | 0.57 (NS) | 3 (8%) | 1 (2%) |

Six serious adverse events are observed during study therapy: 2 blinded FMT, 1 placebo, 3 open-label FMT. One patient with refractory UC on blinded FMT is withdrawn due to clinical and endoscopic deterioration, and underwent colectomy. Three initial placebo-treated patients fail to improve with open-label FMT and require hospitalization for intravenous corticosteroids or anti-TNF therapy.

Multi-donor, intensive-dosing FMT in UC appear to be safe in the short term. Most serious adverse events relate to either corticosteroid-dependent or refractory patients unable to tolerate steroid wean, or patients with moderate to severe colitis. The patient who undergone a colectomy while on FMT demonstrates that a small subset of UC patients may be susceptible to disease worsening with this therapy.

No individual donor or donor batch is significantly associated with the primary outcome, although this particular study is not powered to evaluate this. One of the donor tends to be associated with benefit, 37% of patients with and 18% without this donor achieving the primary outcome (P=0.054). Donor batch does not correlate with the primary endpoint or serious adverse events.

Based on available data and anecdotal experience, the predicted FMT remission rate is 60%, placebo rate is 15%, and dropout rate is 30%. Forty patients per group are required for an 80% probability of demonstrating a difference with a two-sided alpha of 0.05 on intention-to-treat analysis.

All analyses are intention to treat (ITT), including all patients who received at least one study dose. Patients who require increased therapy, breach study protocol, fail to cease corticosteroids by week 8, or terminate the study for any reason are deemed treatment failures. Missing and incomplete data are assigned the worst value in the cohort for statistical analyses.

Descriptive statistics are computed for all variables. Normally distributed continuous data are expressed as mean and standard deviation, and are analyzed using unpaired t-test. Data not normally distributed are expressed as median and interquartile range and are analyzed using Wilcoxon rank sum test. Categorical data are assessed by Chi-square and Fisher's exact tests. Results are expressed as odds ratios with 95% confidence intervals. A p-value of <0.05 is considered significant.

Statistical analyses are performed using SPSS version 23.0 software (Chicago, Ill.).

Example 6. Gastrointestinal Microbiota Analyses

Microbiological analyses are performed on patient, individual donor and FMT batch fecal samples. Samples are stored at −80° C. Fecal bacterial DNA is extracted. The 16S rRNA gene fragment is amplified using the F27 and 519R primers, then is subjected to high throughput sequencing on an Illumina MiSeq platform (2×300 bp chemistry) to determine microbiota diversity and abundance. Raw sequences are analyzed using MOTHUR (Schloss et al. Appl. Environ. Microbiol. 2009; 75:7537-41). Statistical tests are performed on counts and relative abundances.

Diversity ($\alpha$- and phylogenetic) analyses and statistical analyses including principal component analysis (PCA), CLUSTER with SIMPROF testing, permutational MANOVA (PERMANOVA), and PERMDISP are performed on the reads using MOTHUR and Primer-E (Clarke. J. of Ecology 1993; 18(1):117-43). Linear Discriminant Analysis Effect Size (LEfSe) analysis (Segata et al. Genome Biol. 2011; 12:R60) is performed using the Galaxy web application (Goecks et al. Genome Biol. 2010; 11:R86).

Fecal samples are collected from 70 patients. Three hundred and fourteen patient and 113 donor fecal samples (55 individual donor and 58 batch samples) are analyzed. The number of clean sequences obtained per sample is 26976±540 Rarefaction curves suggest that sampling has reached saturation.

Figure 6A:
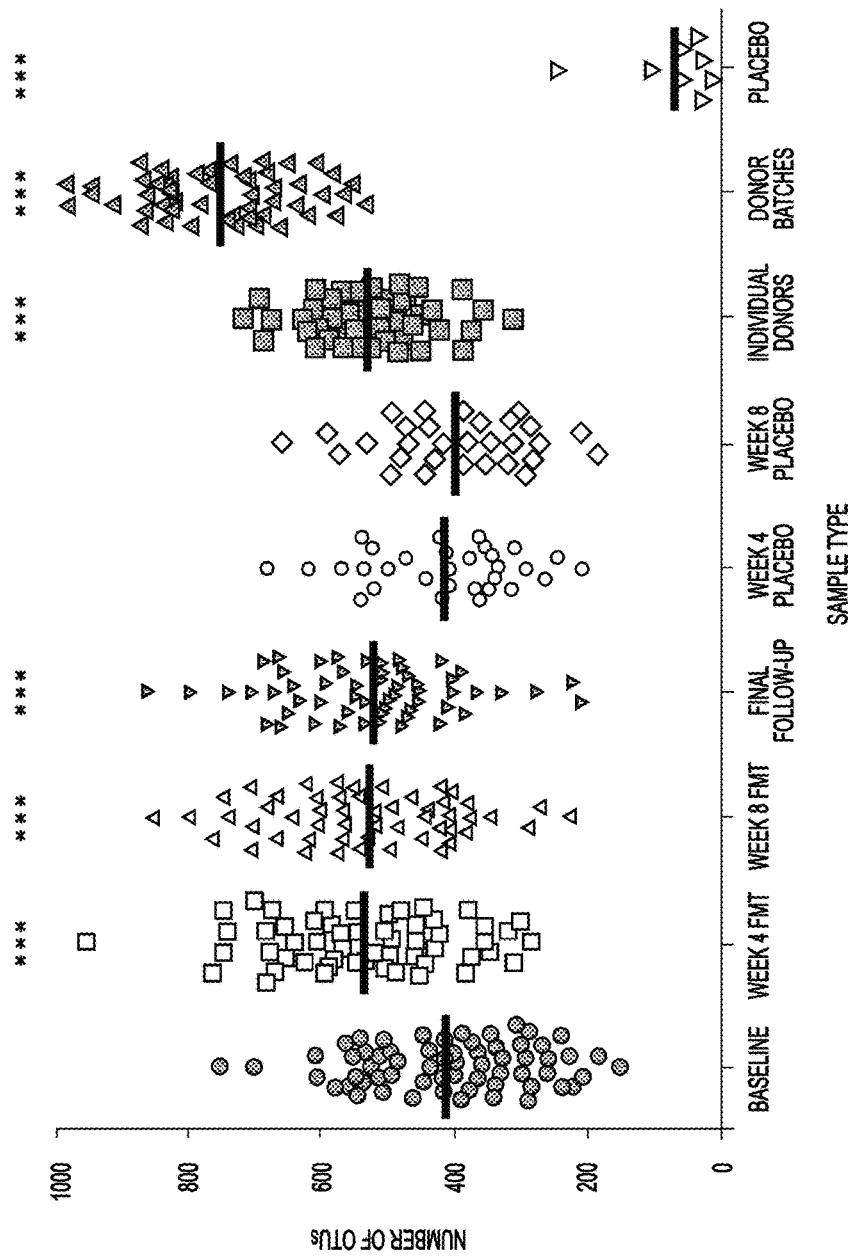
FIG. 6A shows the number of operational taxonomic units (OTUs) per fecal sample in accordance with Example 6 of the present disclosure.
Figure 6B:
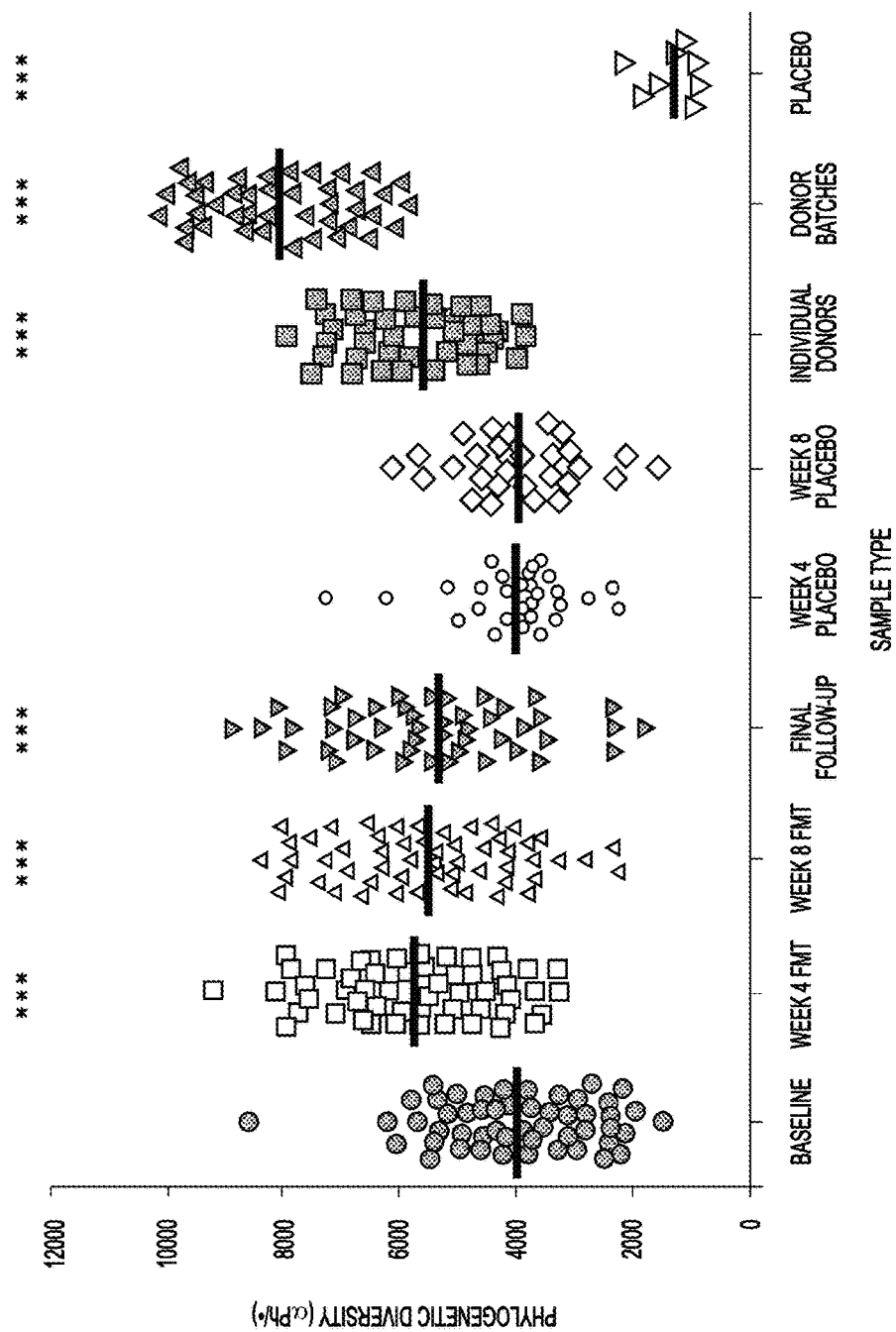
FIG. 6B shows the phylogenetic diversity within each fecal sample in accordance with Example 6 of the present disclosure.

The number of operational taxonomic units (OTUs) and phylogenetic diversity are significantly higher in donor batches than individual donors (FIG. 6A and FIG. 6B). The number of OTUs and phylogenetic diversity of donor samples (batch and individual) are significantly higher than baseline patient samples (FIG. 6A and FIG. 6B). *** in FIG. 6A and FIG. 6B denotes P<0.0001.

OTU number and phylogenetic diversity increase significantly relative to baseline in all FMT-treated patients at 4 and 8 weeks (p<0.0001) and persist 8 weeks post-FMT (p<0.0001) (FIG. 6A and FIG. 6B). Similar patterns are observed for species richness and Shannon's diversity.

Figure 6C:
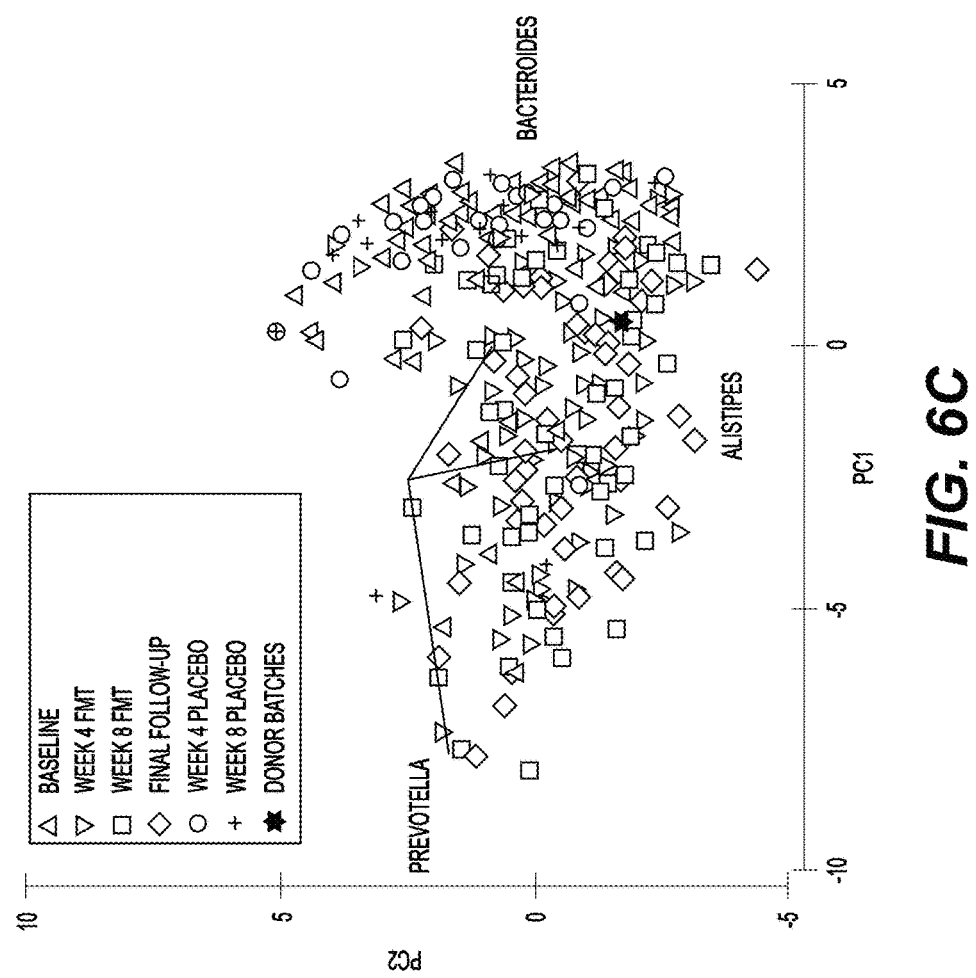
FIG. 6C shows the principal component analysis of fecal samples at the genus taxonomic level in accordance with Example 6 of the present disclosure.

Significant differences in microbial profiles and reduced dispersion levels are observed from OTU to Class taxonomic levels following FMT. PCA confirms the changes in microbial profiles of patients undergoing FMT (FIG. 6C). Patient profiles shift from a dominance of *Bacteroides* to *Prevotella* (FIG. 6C). The shift in microbial profiles of patients undergoing FMT towards the donor is most notable at the OTU level.

Patient baseline samples are compared with week 4, week 8, and 8 weeks post-FMT to identify taxa altered by FMT, and with donor samples to identify OTUs associated with donor batches and those associated with the patient. Two hundred and ninety-five microbial taxa across all taxonomic levels are transplanted with FMT, of which 78 show strong associations (LDA score >3). There is a decrease in patient *Bacteroides* (e.g. OTU 8, 15, 69) and a marked increase in donor *Prevotella* (e.g. OTU 2) and donor *Bacteroides* (e.g. OTU 12, 26, 56) with FMT, independent of clinical outcome. This pattern is more apparent when OTUs are picked at higher resolution.

Figure 6D:
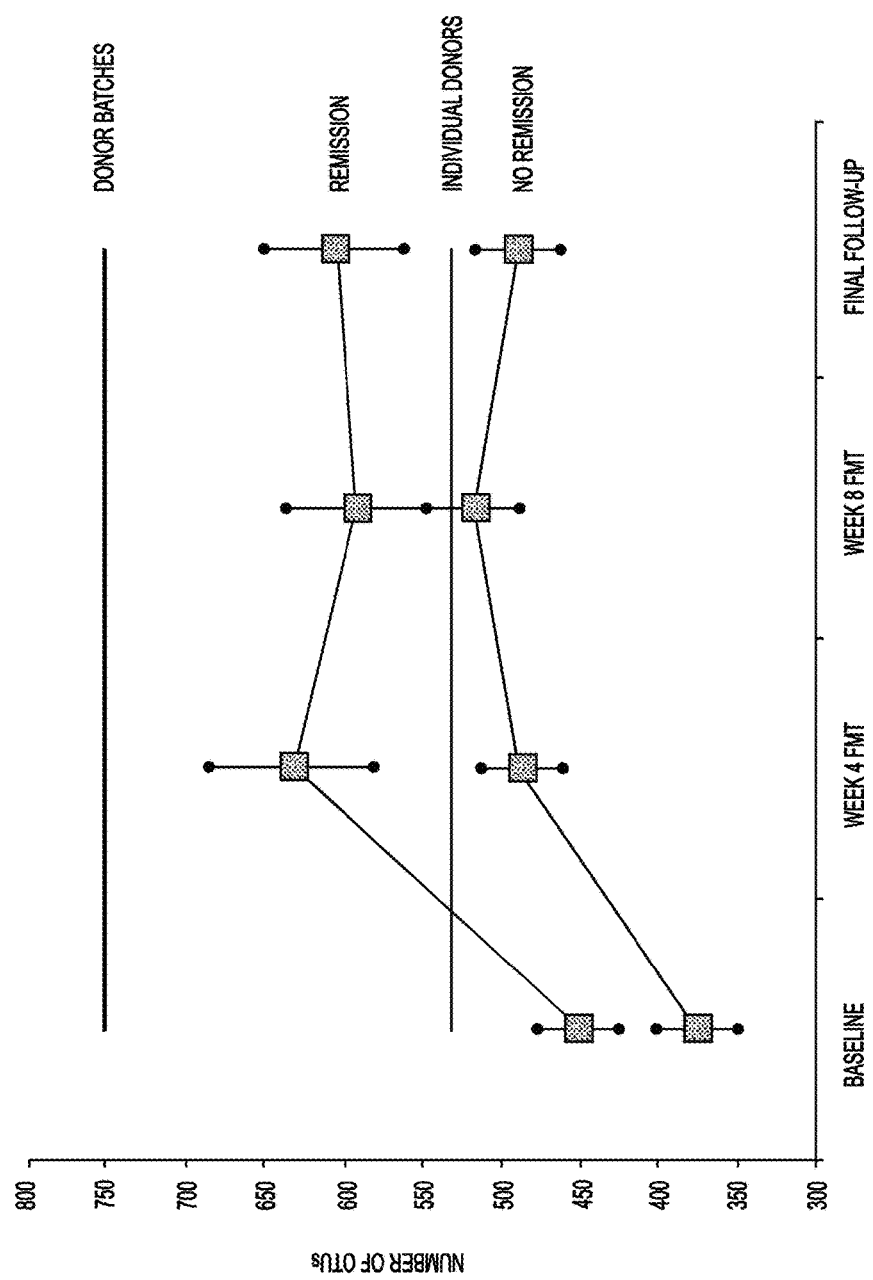
FIG. 6D shows the number of OTUs in blinded study patients on FMT therapy, according to primary outcome, individual donors, and donor batches in accordance with Example 6 of the present disclosure.
Figure 7A:
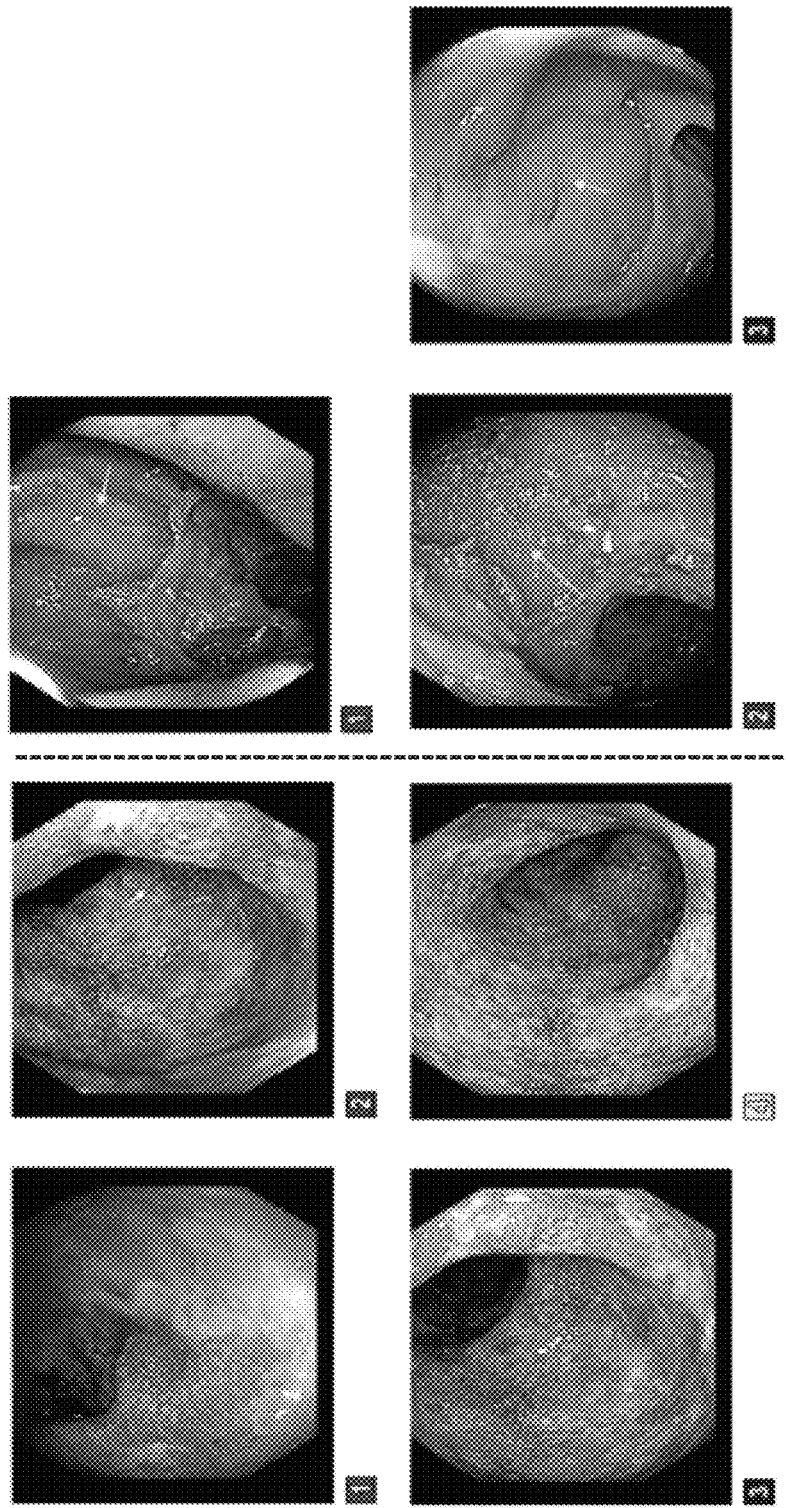
FIG. 7A shows the endoscopy images of (left 1 and 2) marked UC inflammation of the rectum prior to treatment; (right 1) dramatic reduction in inflammation with stool attaching to the mucosa at week 20; (left 3 and 4) marked UC inflammation in the sigmoid colon prior to treatment; and (right 2 and 3) marked reduction in inflammation in the sigmoid colon at week 20.
Figure 7B:
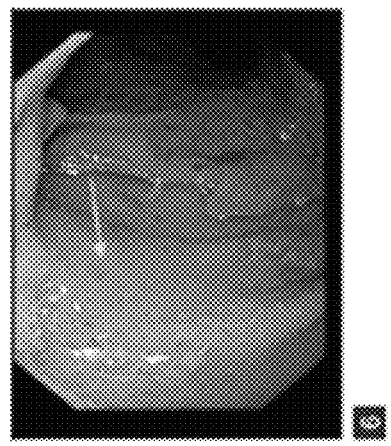
FIG. 7B shows the endoscopy images of (left 7, 8, 9, and 10) inflammation and significant mucus in the traverse colon at week 8 post-treatment; and (right 6) improvement in inflammation at week 20.
Figure 7B:
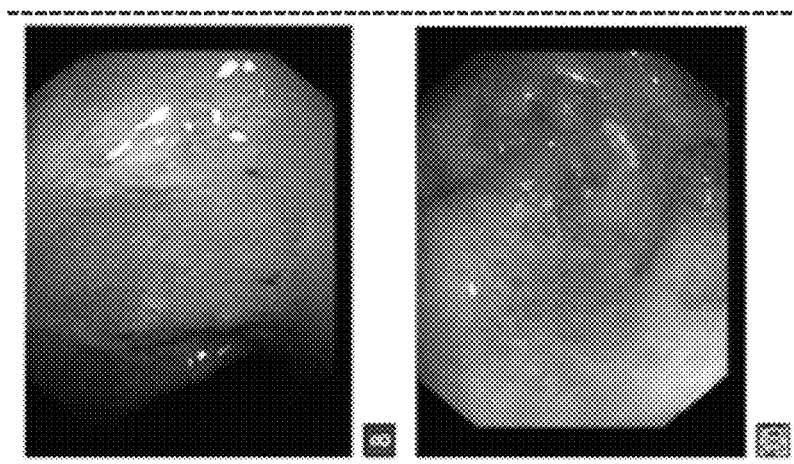
Figure 7B:
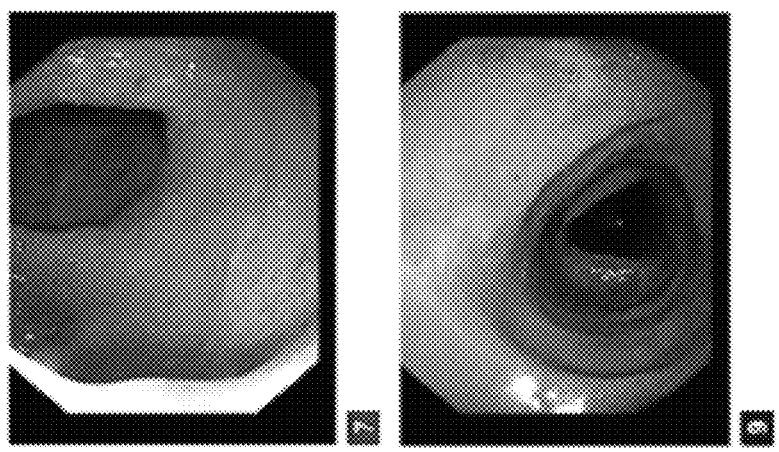

Blinded FMT-treated patients who achieve the primary outcome tend to have higher baseline alpha-diversity than those who do not (P=0.1, FIG. 6D). Blinded FMT-treatment is associated with significantly increased diversity in all patients; however patients who achieve the primary outcome have greater diversity during FMT and 8 weeks post-FMT, achieving levels higher than individual donors though lower than the donor batches (FIG. 6D). Increased $\alpha$-diversity is specific to FMT; three patients who meet the primary outcome on placebo show no change in diversity.

To identify microbial taxa associated with primary outcome on FMT, LEfSe analyses are performed with blinded FMT and open-label FMT patients are stratified. 87 taxa are significantly associated with primary outcome in blinded patients and 46 taxa in open label FMT patients. A range of microbial taxa are associated with remission in the blinded FMT (e.g. *Barnesiella*, *Parabacteroides*, *Clostridium* IV and *Ruminococcus*) and open label FMT patients (e.g. *Blautia*, *Dorea*, *Ruminococcus*2, and *Clostridium* XVIII). Both *Fusobacterium* and *Sutterella* are consistently associated with lack of remission in both blinded and open label FMT patients; for *Fusobacterium* this involves either lack of eradication in patients who do not achieve remission, transplantation into patients without remission, or eradication in patients who achieve remission.

Example 7. Treatment-Naïve Ulcerative Colitis Patient Treated with Oral Fecal Microbiome Therapy A 44-year old treatment-naïve male patient (patient DM) presents with a one year history of diarrhea, blood and mucous in stool, cramping/abdominal pain, and weight loss. The patient experiences severe pain upon defecation, incontinence whilst driving, loss of appetite, nausea, inability to eat spicy foods and fish, brain fog, and weight loss of 16 lbs. The patient also experiences 10-12 bowel movements per day with a consistency of 7 (Bristol), severe bloating, severe abdominal discomfort, and severe urgency. The patient is diagnosed with severe pancolitis. A treatment regimen including acid resistant/delayed release double encapsulated oral capsules containing lyophilized donor-derived non-selected fecal microbiota is used. Briefly, donor stool is collected and homogenized with cryoprotectant and the resulting slurry is lyophilized and encapsulated in DRcaps® capsules containing ~$1.6 \times 10^{11}$ viable cells/capsule. The patient is treated with a total of 404 capsules over a 13-week induction period. During this period, symptom questionnaires are collected and stools are cultured for pathogens to assess efficacy of the LFSM treatment.

The patient's UC symptoms show improvement (see Table 11). By week 8 post-treatment, blood and mucous are barely visible in stool, by week 10 it is nil. The patient's incontinence ceases and bowel motions decrease to 2-3/day with a consistency of 4 (Bristol). With continuing treatment, calprotectin levels decrease from 600 µg/g in week 22, to 344 µg/g in week 26. This confirms an ongoing inflammation reduction which is also shown by endoscopy in FIG. 7. The patient does not report any side-effects relating to the tolerability of the treatment. This case represents a successful treatment of ulcerative colitis (UC) with oral fecal microbiome therapy. In addition to the quality of life (QoL) improvement which result from the patient's UC symptom improvements, there is also a significant increase in energy levels that allows for daily exercise and confidence to recommence work due to reduced incontinence. The patient continues well on maintenance treatment of 4 capsules per day. Oral fecal microbiome therapy is efficacious when treating a treatment-naïve UC patient with pancolitis, resulting in an overall improved QoL.

TABLE 11

Symptoms Pre- and Post- Treatment

| | Pre-Treatment Symptoms | Post-Treatment Symptoms |
|---|---|---|
| Daily BM & Bristol Stool Cart Type | 6-10, BSC - 5/6/7 | 2 BM, BSC - 4/5 |
| Abdominal Pain/Discomfort | 3-4 | 1 |
| Urgency to pass a motion | 4 | 1 |
| Difficulty passing a motion | 2 | 1 |
| Pain during defecation | 3-4 | 1 |
| Bloating | 1 | 1 |
| Constipation | 1 | 1 |
| Diarrheoea | 4 | 1 |
| Blood in stool | 3 | 1 |
| Mucus in stool | 4 | 2 |
| Flatulence | 1 | 1 |
| Nausea | 3 | 1 |
| Fatigue | 2 | 1 |
| General Malaise | 3 | 2 |

1 - none;
2 - Mild;
3 - Moderate;
4 - Severe

Example 8. Ulcerative Colitis Patient Treated with Oral Fecal Microbiome Therapy A 31-year old patient (patient TD) is treated with fecal microbiome therapy. A treatment regimen including acid resistant/delayed release double encapsulated oral capsules containing lyophilized donor-derived non-selected fecal microbiota is used. The patient's symptoms include of 4 bowel movements per day with a consistency of 2, moderate bloating, moderate abdominal discomfort, mild urgency, and feelings of pins and needles in legs and fatigue. The patient is placed on a 6 week treatment protocol with one fecal microbiome therapy liquid colonoscopic infusion and 1-2 rectal enema infusions per week during the induction period. The patient takes 4 capsules per day for 4 weeks during the maintenance period. The patients symptoms of bloating decrease and symptoms of abdominal discomfort and urgency disappear. The patient experiences one bowel movement per day with a consistency of 3. The patient also experiences mild flatulence and general malaise. Two weeks after capsule treatment the patient has a calprotectin reading of 243 µg/g. Three weeks from the first calprotectin test and 4 weeks from the initial capsule intake, the patient's calprotectin level decreases to 88 µg/g.

As various modifications could be made in the constructions and methods herein described and illustrated without departing from the scope of the disclosure, it is intended that all matter contained in the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entirety.

The invention claimed is:

1. A method for treating ulcerative colitis (UC) in a subject in need thereof comprising treating the subject with a treatment regimen comprising the administration of an oral or rectal pharmaceutical composition comprising viable non-pathogenic fecal bacteria comprising *Clostridium*, *Ruminococcus*, and *Dorea*, for at least 4 weeks and at least once per week, wherein the viable non-pathogenic fecal bacteria are from multiple donors having no history or current symptoms of gastrointestinal disease.

2. The method of claim 1, wherein the treatment regimen achieves a primary outcome rate of at least two fold higher relative to a primary outcome rate from placebo, wherein the primary outcome comprises a steroid-free clinical remission at the end of the treatment regimen, wherein the clinical remission is defined as a total Mayo score of 2 or lower with all sub-scores of 1 or lower.

3. The method of claim 2, wherein the treatment regimen is capable of achieving a primary outcome rate of at least 25%.

4. The method of claim 2, wherein the primary outcome further comprises an endoscopic remission or response, wherein the endoscopic remission or response is defined as a reduction of at least 1 point from baseline in Mayo endoscopy score.

5. The method of claim 1, wherein the treatment regimen comprises administering the pharmaceutical composition for at least 8 weeks and at least three times per week.

6. The method of claim 1, wherein the treatment regimen comprises administering the pharmaceutical composition for at least 8 weeks and at least five times per week.

7. The method of claim 1, wherein the viable non-pathogenic fecal bacteria comprise cultured bacteria.

8. The method of claim 1, wherein the viable non-pathogenic fecal bacteria are live fecal bacteria.

9. The method of claim 1, wherein the viable non-pathogenic fecal bacteria are in a spore form.

10. The method of claim 1, wherein the treatment regimen is capable of achieving a clinical remission sustaining rate of at least 40% at 8 weeks after the completion of the treatment regimen.

11. The method of claim 1, wherein the treatment regimen is capable of achieving a steroid-free clinical response rate of at least two fold higher relative to a steroid-free clinical response rate from placebo, wherein the clinical response is defined as a total Mayo score decrease of 3 or higher or a 50% or higher reduction from baseline in combined score for rectal bleeding and stool frequency.

12. The method of claim 11, wherein the treatment regimen is capable of achieving a steroid-free clinical response rate of at least 50%.

13. The method of claim 1, wherein the treatment regimen is capable of achieving an endoscopic response rate of at least two fold higher relative to an endoscopic response rate from placebo, wherein the endoscopic response is defined as a total UCEIS score decrease of 3 or higher or a 50% or higher reduction from baseline.

14. The method of claim 13, wherein the treatment regimen is capable of achieving an endoscopic response rate of at least 30%.

15. The method of claim 1, wherein the method further comprises determining the level of one or more bacteria selected from the group consisting of *Fusobacterium, Sutterella, Barnesiella, Parabacteroides, Clostridium* IV, *Ruminococcus, Blautia, Dorea, Ruminococcus*2, and *Clostridium* XVIII in the subject's gut.

16. A method for treating ulcerative colitis (UC) in a subject in need thereof comprising treating the subject with a treatment regimen comprising the administration of an oral or rectal pharmaceutical composition comprising viable non-pathogenic fecal bacteria comprising *Clostridium, Ruminococcus*, and *Dorea*, for at least 4 weeks and at least once per week, wherein the pharmaceutical composition comprises higher microbial heterogeneity than a fecal microbe composition from a single donor having no history or current symptoms of gastrointestinal disease.

17. The method of claim 16, wherein the treatment regimen achieves a primary outcome rate of at least two fold higher relative to a primary outcome rate from placebo, wherein the primary outcome comprises a steroid-free clinical remission at the end of the treatment regimen, wherein the clinical remission: is defined as a total Mayo score of 2 or lower with all sub-scores of 1 or lower.

18. The method of claim 17, wherein the treatment regimen is capable of achieving a primary outcome rate of at least 25%.

19. The method of claim 17, wherein the primary outcome further comprises an endoscopic remission or response, wherein the endoscopic remission or response is defined as a reduction of at least 1 point from baseline in Mayo endoscopy score.

20. The method of claim 16, wherein the treatment regimen comprises administering the pharmaceutical composition for at least 8 weeks and at least three times per week.

21. The method of claim 16, wherein the viable non-pathogenic fecal bacteria comprise cultured bacteria.

22. A method for treating ulcerative colitis (UC) in a subject in need thereof comprising treating the subject with a treatment regimen comprising the administration of an oral or rectal pharmaceutical composition comprising viable non-pathogenic fecal bacteria comprising *Clostridium, Ruminococcus*, and *Dorea*, for at least 4 weeks and at least twice per week, wherein the subject has no concomitant corticosteroid use during the method and wherein the subject has no steroid use within at least one week prior to commencing the method.

23. The method of claim 22, wherein the treatment regimen achieves a primary outcome rate of at least two fold higher relative to a primary outcome rate from placebo, wherein the primary outcome comprises a steroid-free clinical remission at the end of the treatment regimen, wherein the clinical remission is defined as a total Mayo score of 2 or lower with all sub-scores of 1 or lower.

24. The method of claim 23, wherein the treatment regimen is capable of achieving a primary outcome rate of at least 25%.

25. The method of claim 22, wherein the viable non-pathogenic fecal bacteria are not from a single donor.

26. The method of claim 22, wherein the treatment regimen comprises administering the pharmaceutical composition comprising viable non-pathogenic fecal bacteria for at least 8 weeks and at least three times per week.

27. The method of claim 22, wherein the treatment regimen comprises administering the pharmaceutical composition comprising viable non-pathogenic fecal bacteria for at least 8 weeks and at least five times per week.

28. The method of claim 22, wherein the viable non-pathogenic fecal bacteria comprise cultured bacteria.

29. The method of claim 1, wherein the pharmaceutical composition comprising viable non-pathogenic fecal bacteria further comprises viable non-pathogenic fecal bacteria selected from the group consisting of *Barnesiella, Parabacteroides, Clostridium* IV, *Blautia, Ruminococcus*2, and *Clostridium* XVIII.

30. The method of claim 1, wherein the viable non-pathogenic fecal bacteria comprise a microbiota of a stool of a healthy donor.

31. The method of claim 16, wherein the pharmaceutical composition comprising viable non-pathogenic fecal bacteria further comprises viable non-pathogenic fecal bacteria selected from the group consisting of *Barnesiella, Parabacteroides, Clostridium* IV, *Blautia, Ruminococcus*2, and *Clostridium* XVIII.

32. The method of claim 16, wherein the viable non-pathogenic fecal bacteria comprise a microbiota of a stool of a healthy donor.

33. The method of claim 22, wherein the pharmaceutical composition comprising viable non-pathogenic fecal bacteria further comprises viable non-pathogenic fecal bacteria selected from the group consisting of *Barnesiella, Parabacteroides, Clostridium* IV, *Blautia, Ruminococcus*2, and *Clostridium* XVIII.

34. The method of claim 22, wherein the viable non-pathogenic fecal bacteria comprise a microbiota of a stool of a healthy donor.

35. The method of claim 1, wherein the pharmaceutical composition is an oral pharmaceutical composition.

36. The method of claim 16, wherein the pharmaceutical composition is an oral pharmaceutical composition.

37. The method of claim 22, wherein the pharmaceutical composition is an oral pharmaceutical composition.

* * * * *